(12) United States Patent
Manetti et al.

(10) Patent No.: US 11,707,239 B2
(45) Date of Patent: *Jul. 25, 2023

(54) RADIOLOGICAL IMAGING DEVICE FOR LOWER LIMBS

(71) Applicant: Imaginalis S.r.l., Sesto Fiorentino (IT)

(72) Inventors: Leonardo Manetti, Montevarchi (IT); Massimiliano Leonori, Lucca (IT); Damiano Fortuna, Rignano Sull'arno (IT)

(73) Assignee: IMAGINALIS S.R.L., Sesto Fiorentino (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/839,471

(22) Filed: Jun. 13, 2022

(65) Prior Publication Data

US 2022/0304639 A1    Sep. 29, 2022

Related U.S. Application Data

(63) Continuation of application No. 16/827,273, filed on Mar. 23, 2020, now Pat. No. 11,357,460, which is a
(Continued)

(30) Foreign Application Priority Data

Feb. 23, 2015   (IT) ........................ MI2015A000264

(51) Int. Cl.
  *A61B 6/04*  (2006.01)
  *G01T 1/166*  (2006.01)
  *A61B 6/00*  (2006.01)

(52) U.S. Cl.
  CPC .............. *A61B 6/4435* (2013.01); *A61B 6/04* (2013.01); *A61B 6/4405* (2013.01);
(Continued)

(58) Field of Classification Search
  CPC ....... A61B 6/4435; A61B 6/04; A61B 6/4405; A61B 6/4452; A61B 6/508; A61B 6/466;
(Continued)

(56) References Cited

U.S. PATENT DOCUMENTS

2006/0029181 A1    2/2006  Chen et al.
2006/0245539 A1 *  11/2006  Sukovic ................. A61B 6/466
                                                        378/20
(Continued)

FOREIGN PATENT DOCUMENTS

WO   WO-2012073109 A1 *  6/2012  ........... A61B 5/1036
WO   2015/054466 A1   4/2015

OTHER PUBLICATIONS

"Idle Wheel" Definition, Vocabulary.com, obtained from https://www.vocabulary.com/dictionary/idle%20wheel on Oct. 4, 2022 (Year: 2022).*

Primary Examiner — David P Porta
Assistant Examiner — Jeremy S Valentiner
(74) Attorney, Agent, or Firm — Steptoe & Johnson LLP; Carl B. Wischhusen

(57) ABSTRACT

A radiological imaging device configured to analyze a limb includes a first module that includes a source configured to emit radiation, a second module that includes a detector configured to receive radiation from the source that has passed through the limb, a control station connected to the first and second modules for controlling movement of the first and second modules and acquiring images from the second module, and a platform having an outer support surface to support the first and second modules. The control station includes a casing and a connecting member that is connected to the casing to attach the platform. The platform is suitable to rotate around an axis approximately parallel to the outer surface.

12 Claims, 10 Drawing Sheets

Related U.S. Application Data continuation of application No. 15/550,417, filed as application No. PCT/IB2016/050929 on Feb. 22, 2016, now Pat. No. 10,595,801.

(52) U.S. Cl.
CPC ............ *A61B 6/4452* (2013.01); *A61B 6/508* (2013.01); *G01T 1/166* (2013.01); *A61B 6/466* (2013.01); *A61B 6/487* (2013.01); *A61B 2562/0247* (2013.01)

(58) Field of Classification Search
CPC .. A61B 6/487; A61B 2562/0247; G01T 1/166
See application file for complete search history.

(56) References Cited

U.S. PATENT DOCUMENTS

| | | | |
|---|---|---|---|
| 2008/0319300 A1* | 12/2008 | Do-Huu | A61B 6/4405 600/407 |
| 2009/0185663 A1* | 7/2009 | Gaines, Jr. | A61B 6/0487 5/601 |
| 2010/0278300 A1 | 11/2010 | Yorkston et al. | |
| 2013/0089179 A1 | 4/2013 | Kenny | |
| 2014/0376684 A9* | 12/2014 | Litzenberger | A61B 6/527 378/4 |
| 2015/0313557 A1* | 11/2015 | Mackie | A61B 6/4429 378/14 |
| 2016/0242719 A1* | 8/2016 | Yorkston | A61B 6/508 |
| 2017/0135652 A1 | 5/2017 | DiRisio | |

\* cited by examiner

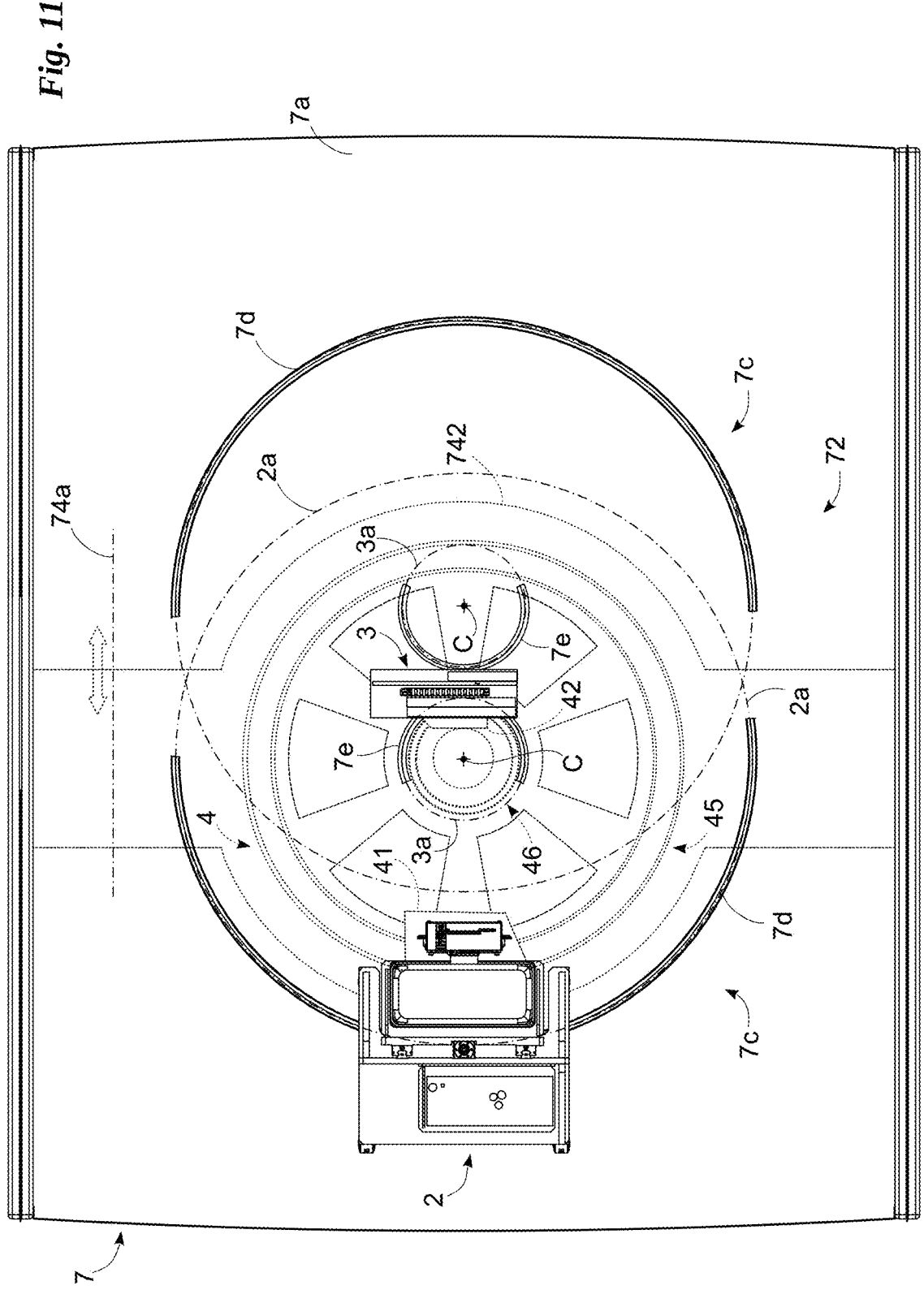

RADIOLOGICAL IMAGING DEVICE FOR LOWER LIMBS

CROSS-REFERENCE TO RELATED APPLICATIONS

This application is a continuation of U.S. patent application Ser. No. 16/827,273, filed Mar. 23, 2020, now U.S. Pat. No. 11,357,460, which is a continuation of U.S. patent application Ser. No. 15/550,417, filed Aug. 11, 2017, now U.S. Pat. No. 10,595,801, which is a 371 Application of PCT/IB2016/050929, filed Feb. 22, 2016, which claims priority from Italian Application No. MI2015A000264, filed Feb. 23, 2015. This application claims priority from Application Ser. No. 15/550,417, PCT/IB2016/050929 and MI2015A000264 each of which is incorporated herein by reference in its entirety.

DESCRIPTION

The present invention relates to a radiological imaging device for limbs of the type specified in the preamble of the first claim.

In particular, the device is suitable to be used in the medical sphere to acquire images of the lower limbs of human beings and in the veterinary sphere to acquire images of the front and/or rear limbs.

BACKGROUND

The radiological imaging devices currently known of are fitted with a gantry and a support structure for the patient.

The gantry has an annular casing defining, in the center, an area of analysis inside which the sensor and the source and the various movement and control members of the source and the detector are placed.

The support is a horizontal bed which the patient lies on and which is suitable to be placed in the area of analysis enabling the limbs to be placed in said area and, thus, between the source and detector.

The prior art mentioned above has several significant drawbacks.

The first drawback is in the substantial impossibility of performing tomography or other imaging only of the limb concerned from any angle.

In fact, the patient's limbs are both located within the area of analysis and, therefore, the rotation of the source and detector imposes the acquisition of images of both limbs.

To resolve this problem support parts have been designed on which to rest only the limb to be analyzed while leaving the other limb outside the gantry or which allow the positioning of the limbs in different positions.

Patents CH 692378 documents, US 2011/231995, U.S. Pat. No. 6,378,149 describe examples of such supports.

Such supports, while reducing such drawback, do not permit an optimal and complete acquisition of the limb.

These are utilizable almost exclusively in the human medical sphere, while they cannot be used in veterinary medicine and, most importantly, with horses or other animals of large or medium size.

In fact, the significant weight and size of these animals cause considerable positioning difficulties of the animal on the support and often require both the use of sedatives to put the animal to sleep and the use of cranes or other means to move the animal.

Another drawback is determined by the fact that these supports impose unnatural positions of the limbs on the patient and are thus uncomfortable to maintain for the entire acquisition time.

This drawback is particularly evident in tomography where, due to its long duration, movements of the limbs may occur such as to require repetition of the acquisition.

Another drawback of no less importance peculiar to all the devices described above is that on account of their large dimensions they are impossible to transport and thus require that the animal be brought to the appropriate facilities.

In this situation the technical purpose of the present invention is to devise a radiological imaging device able to substantially overcome the drawbacks mentioned above.

SUMMARY

Within the sphere of said technical purpose one important purpose of the invention is to have an imaging device that produces a high-quality radiographic image in a simple and fast manner regardless of the physical characteristics of the patient or the portion of limb concerned. Briefly, and in general terms, various embodiments are directed to a radiological imaging device for analyzing a limb of a patient, where the features of different embodiments are modular. The radiological imaging device includes a platform having an outer support surface and an inner volume. The device also includes a first module having a source suitable to emit radiation and a second module having a detector suitable to receive the radiation. The first and second modules are disposed on the outer support surface of the platform. The radiological imaging device also includes a drive unit connected to the first and second modules. The drive unit may be housed within the inner volume of the platform, and the drive unit controls the movement of the first and second modules placed on the outer support surface. Also, the radiological imaging device includes at least one attachment to constrain the first and second modules to the drive unit.

In one embodiment, the at least one attachment of the radiological imaging device defines an engagement position. In the engagement position, the at least one attachment constrains the drive unit to the first and second modules to allow the drive unit to move the first and second modules. The at least one attachment also may define a disengagement position. In the disengagement position, the at least one attachment does not constrain the drive unit to the first and second modules to prevent the drive unit from moving the first and second modules.

In certain embodiments of the radiological imaging device, the drive unit may include a first circular guide defining a first drag trajectory and a second circular guide substantially concentric with the first circular guide. The second circular guide may define an axis of rotation and a second drag trajectory distinct from the first drag trajectory. The drive unit may include a first slider that moves along the first circular guide and a second slider that moves along the second circular guide.

In these embodiments, the at least one attachment may include a first attachment constrained to the first slider and suitable to protrude from the platform and engage the first module. The first slider attached to the first module can then move or drag the first module along the first circular guide. The at least one attachment also may include a second attachment constrained to the second slider and suitable to protrude from the platform and engage the second module.

The second slider attached to the second module can then move or drag the second module along the second circular guide.

In another embodiment of the radiological imaging device, the radius of the first circular guide may be substantially between 6 dm and 8 dm. Also, the radius of the second circular guide may be substantially between 1 dm and 2 dm.

In yet another embodiment of the radiological imaging device, the outer support surface includes two analysis areas. The analysis centers of the two analysis areas may have a mutual distance between approximately 1.5 dm and 4 dm.

In the embodiment of the radiological imaging device, wherein the outer support surface includes a plurality of analysis areas, the platform may include a conveyor housed in the inner volume. The conveyor moves the drive unit with respect to the outer support surface defining a plurality of acquisition positions. In each of these acquisition positions, the rotation axis passes substantially through the analysis center of one of the plurality of analysis areas.

The outer support surface of the platform, in one embodiment, may include an outer through opening defining a first acquisition path of the first module and through which the first attachment protrudes from the platform. The outer support surface may also include an inner through opening defining a second acquisition path of the second module, through which the second attachment protrudes from the platform. The inner through opening may be substantially concentric with the outer through opening defining a center of analysis. The outer support surface may include at least one analysis area substantially delimited by one of the outer through opening and the inner through opening. The outer through opening and the inner through opening may have an angular extension substantially between 190° and 250°.

In yet another embodiment, the radiological imaging device may include a control station. The control station commands the operation of the radiological imaging device. Further, the control station includes a casing defining the outer surface of the control station. The control station may have at least one coupling to constrain the first and second modules and a connecting member of the platform to the casing.

In certain embodiments, the radiological imaging device may include a connection apparatus at least partially housed in the inner volume of the platform. The connection apparatus allows a passage of at least data or power between the control station and the first and second modules. and the connection apparatus includes a connector suitable to carry at least data or power from the control station to the drive unit.

In yet another embodiment, the radiological imaging device includes at least one pressure sensor positioned on the platform. The pressure sensor detects a change or shift in weight on the platform. More particularly, the pressure sensor may detect a change of shift in weight in the analysis area of the device. Any change of shift in weight detected by the pressure sensor can a transition from the engaged position into the disengaged position of the at least one attachment. Once the pressure sensor detects a stable weight distribution on the platform for a certain amount of time, the pressure sensor can trigger a transition from the disengaged position to the engaged position of the at least one attachment. In certain embodiments, the pressure sensors are in communication with the control unit, which causes the at least one attachment to transition from the disengaged position to the engaged position, and vice versa.

Other features and advantages will become apparent from the following detailed description, taken in conjunction with the accompanying drawings, which illustrate by way of example, the features of the various embodiments.

Another important purpose of the invention is to obtain an imaging device which allows the patient to adopt a comfortable position and which is thus easy to maintain for the entire period of the analysis.

The technical purpose and specified aims are achieved by a radiological imaging device as claimed in the appended claim 1.

Preferred embodiments are evident from the dependent claims.

BRIEF DESCRIPTION OF THE DRAWINGS

The characteristics and advantages of the invention are clearly evident from the following detailed description of a preferred embodiment thereof, with reference to the accompanying drawings, in which:

FIG. 11 shows an assembly of the radiological imaging device.

DETAILED DESCRIPTION

Figure 1:
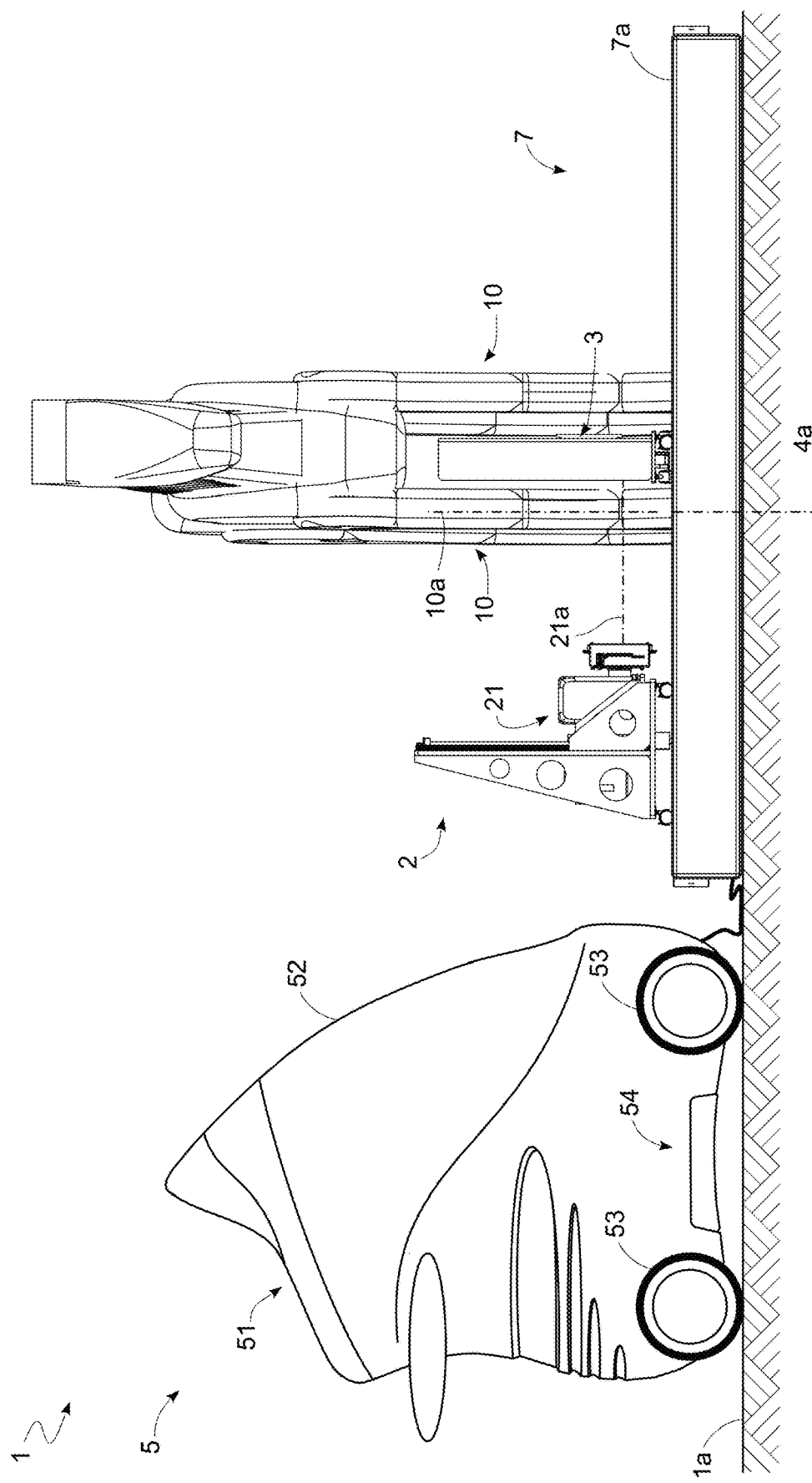
FIG. 1 shows a radiological imaging device according to the invention.
Figure 2:
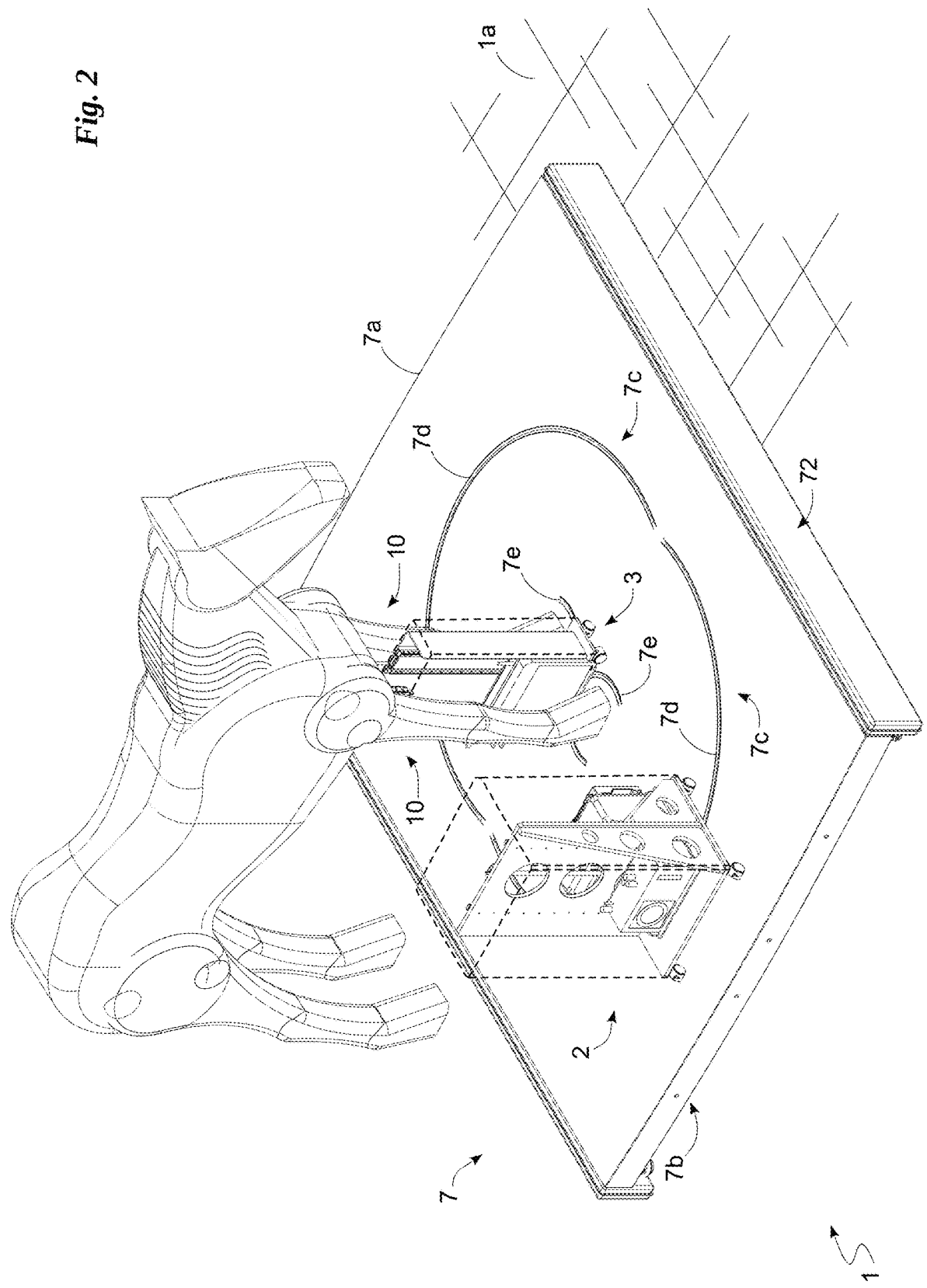
FIG. 2 shows part of the device in FIG. 1.

Herein, the measures, values, shapes and geometric references (such as perpendicularity and parallelism), when used with words like "about" or other similar terms such as "approximately" or "substantially", are to be understood as except in the case of measurement errors or inaccuracies due to production and/or manufacturing errors and, above all, except for a slight divergence from the value, measure, shape or geometric reference which it is associated with. For example, said terms, if associated with a value, preferably indicate a divergence of not more than 10% of said value.

In addition, where used, terms such as "first", "second", "upper", "lower", "main" and "secondary" do not necessarily refer to an order, a priority relationship or relative position, but may simply be used to more clearly distinguish different components from each other.

Except where specified otherwise, as evidenced by the discussions below, it should be noted that in the course of specific discussions using terms such as "processing", "computer", "computing", "evaluation", or the like, reference is made to the action and/or processes of a computer or calculation system, or similar electronic calculation device, which handle and/or process data represented as physical, electronic, sizes of logs of computer systems and/or memories in other data similarly represented as physical quantities inside the records of the computer system, logs or other information storage, transmission or display devices.

With reference to said drawings (FIGS. 1-11), reference numeral 1 globally denotes the radiological imaging device for limbs according to the invention.

The device 1 is suitable for use in the veterinary and/or human field, to acquire radiological images of a limb 10 practically defining a barycentric longitudinal axis 10a. In detail, it is suitable to perform radiological imaging of the lower limbs of a human patient and of the front/rear limbs of an animal patient. More specifically, the imaging device 1 is utilizable in the veterinary sphere for producing radiological images of the front/rear limbs.

The radiological imaging device 1 is suitable to perform at least one of the following: radiography, computerized tomography, and fluoroscopy. Preferably, it can perform both an X-ray, a computerized tomography, and a fluoroscopy.

The imaging device 1 comprises, in brief, a first module 2 comprising a source 21 suitable to emit radiation defining an emission axis 21a; a second module 3 suitable to be placed on the opposite side to the first module 2 with respect to the limb 10 being analyzed and comprising a detector 31 suitable to receive the radiation after it has passed through the limb 10 being analyzed; a drive unit 4 of the modules 2 and 3; a control station 5 of at least the acquisition and the movement of the modules 2 and 3; a connection apparatus 6 suitable to permit a data and/or power exchange between the modules 2 and 3 and the station 5; and a platform 7 suitable to be supported on a floor surface 1a and defining an outer support surface 7a for at least one limb 10 and the modules 2 and 3 and an inner housing 7b for at least the unit 4.

The modules 2 and 3 are preferably supported by gravity on the surface 7a and are suitable to slide on the surface 7a along at least one acquisition path (the paths may follow any shaped path) preferably passively. They are therefore devoid of independent moving means along the surface 7a and, therefore, movable exclusively along said surface by means of the unit 4 and/or manually by the operator.

In particular, the first module 2 is suitable to be moved along a first acquisition path 2a preferably approximately circular; the second module 3 is suitable to slide along a second acquisition path 3a preferably substantially circular.

The paths 2a and 3a have distinct radii.

The second acquisition path 3a has an approximately distinct radius and, to be precise, approximately less than the first acquisition path 2a so that the second module 3 and, thus the detector 31 are at a distance measured along the emission axis 21a from the limb 10 being analyzed, approximately less than that of the first module 2 and thus of the source 21.

In particular, the radius of the first path 2a is approximately greater than 3 dm, in detail, approximately between 5 dm and dm 12 and, in more detail, approximately between 6 dm and 9 dm. Preferably, the radius of the outer through opening 7d is substantially equal to 7 dm.

The radius of the second acquisition path 3a is approximately less than 5 dm, in detail, approximately less than 3 dm and, in more detail, approximately between 2 dm and 1 dm. Preferably the radius of the second acquisition path 3a is substantially between 1.5 dm and 1.6 dm.

The first module 2 has a height, measured perpendicular to the surface 7a, a width, measured parallel to the surface 7a and perpendicular to the emission axis 21a, and a thickness, measured along the emission axis 21a, respectively approximately less than 12 dm, 10 dm and 10 dm.

In particular, the height is substantially less than 10 dm and in particular substantially between 8 dm and 7 dm.

The width is approximately less than 7.5 dm and more in particular approximately between 5.5 dm and 4.5 dm.

The width is approximately less than 7.5 dm and more in particular approximately between 6 dm and 5 dm.

The first module 2 (FIG. 6) comprises a source 21 suitable to emit radiation (X-rays) defining an emission axis 21a preferably substantially parallel to the outer surface 7a; a first translator 22 suitable to translate at least the source 21 along a first translation axis 22a preferably approximately perpendicular to the surface 7a; a first carriage 23 to which the source 21 and translator 22 are constrained and suitable to rest on the outer surface 7a; and a first casing 24 defining, together with the first carriage 23 a first containment space for at least the source 21 and the first translator 22.

The first translation axis 22a is approximately perpendicular to the emission axis 21a.

The first carriage 23 is fitted with idler wheels or other means suitable to permit the first module 2 to be idle in relation to the platform 7, i.e. able to slide idly along the surface 7a.

The first casing 24 is in radiolucent material, such as a polymer, in particular, acrylonitrile butadiene styrene (ABS) so as to be crossed by the radiation emitted by the source 21. Preferably, it is at least partially in a radiolucent and damper material (foam) so as to be able to absorb impacts or other external stresses. Additionally, the first module 2 includes, housed in the first volume, at least one of the following: a cooling system 25 of the source 21; a collimator; a first linear actuator suitable to move the source 21 along the emission axis 21a varying the distance of the source 21 from the second module 3, and thus from the limb 10 being analyzed.

Preferably, the first module 2 has at least the cooling system 25 and the collimator. Lastly, it may provide for a cable holder chain suitable to enable electrical/data cables and/or pipes of the cooling system 25 to follow the source 21 during its translation along the axis 22a.

The cooling system 25 is integral with the source 21 so that the first translator 22 simultaneously translates the source 21 and the system 25.

The collimator, also integral with the source 21, is suitable to vary the direction and/or extent of the radiation for example creating a "fan beam" or "cone beam" tomography or a linear X-ray.

The second module 3 is suitable to place itself between two limbs 10 (such as the lower limbs 10 of a human patient or the front or rear limbs 10 of a horse or other animal) so that only the limb 10 being analyzed is between the modules 2 and 3.

It has a width, suitable to be calculated along the emission axis 21a less than the distance between the limbs 10, i.e. in the case of a horse or the like, than the minimum distance value between the carpals/metacarpals/fetlocks of the front and rear limbs. Said width is substantially less than 3 dm, in particular 2 dm and, more specifically, 1.5 dm.

The second module 3 has a height, measured perpendicular to the surface 7a, a width, measured parallel to the surface 7a and perpendicular to the emission axis 21a, and a thickness, measured along the emission axis 21a, respectively approximately less than 12 dm, 10 dm and 4 dm.

In particular; the height is substantially less than 10 dm and in particular substantially between 8 dm and 7 dm.

The width is approximately less than 7.5 dm and more in particular approximately between 5 dm and 4 dm.

The thickness is substantially less than 3 dm and more in particular approximately between 1.5 dm and 2 dm.

The second module 3 (FIG. 7) includes a detector 31 suitable to receive the radiation after it has crossed the limb 10 being analyzed; a second translator 32 suitable to translate the detector 31 along a second translation axis 32a preferably substantially perpendicular to the surface 7a; a second carriage 33 to which the detector 31 and the second translator 32 are constrained and suitable to rest on the outer surface 7a; and a second casing 34 defining, together with the second carriage 33 a second containment space for at least the detector 31 and the second translator 32.

The detector 31 is suitable to perform at least one of the following: radiography, computerized tomography, and fluoroscopy. In detail, it can perform an X-ray, computerized tomography, and fluoroscopy.

The detector 31 comprises a matrix sensor and, in detail, a flat panel display.

The second axis 32a is approximately perpendicular to the emission axis 21a. Appropriately, the axes 22a and 32a are approximately parallel to each other and, to be precise, to the longitudinal axis 10a of the limb being analyzed.

The second carriage 33 provides for idler wheels or other means suitable to permit the second module 3 to be idle in relation to the platform 7, i.e. able to slide idly along the surface 7a.

The second casing 34 is made of polymer material, preferably of acrylonitrile butadiene styrene (ABS) or other radiolucent material so as to be crossed by the radiation emitted by the source 21. Preferably, it is at least partially made of foam or a radiolucent and damper material so as to be able to absorb impacts or other external stresses.

Additionally, the second module includes 3, positioned in the second casing 34 and integral with the detector 31, at least one of the following: a battery 35 suitable to power at least the detector 31 and the second translator 32; and a second linear actuator suitable to translate the sensor 31 along the emission axis 21a by varying the distance between the sensor 31 and the limb 10 being analyzed.

Lastly, it may provide for a cable holder chain suitable to enable electrical/data cables to follow the detector 31 during its translation along the axis 22a.

The modules 2 and 3 are passive, i.e. devoid of drives and movable only by the operator and/or by the unit 4.

The drive unit 4 is approximately entirely placed in the inner housing 7b.

It comprises at least one circular guide defining at least a circular drag trajectory of the rotation axis 4a; at least one slider suitable to slide along said circular guide and to be constrained to the modules 2 and 3; and at least one mover suitable to control the movement of the slider and thus of the modules 2 and 3.

The rotation axis 4a is approximately perpendicular to the outer surface 7a and thus to the emission axis 21a, preferably, approximately parallel to the translation axes 22a and 32a, and more preferably, approximately concentric to the longitudinal axis 10a of the limb 10 being analyzed.

In particular, the drive unit 4 provides for a first slider 41 and a second 42 slider suitable to slide along said circular guide and to be respectively constrained to the first module 2 and to the second module 3; a first mover 43 and a second mover 44 suitable to control the movement respectively of the first slider 41 and of the second slider 42.

More specifically, the drive unit 4 (FIGS. 4, 5 and 9) provides for two different guides, i.e. a first circular guide 45 defining a first circular drag trajectory 45a with axis 4a and along which the first slider 41 slides dragging the first module 2; a second circular guide 46 defining a second circular drag trajectory 46a with axis 4a, distinct from the first drag trajectory 45a and along which the second slider 42 slides dragging the second module 3.

The second drag trajectory 46a is substantially concentric with the first guide 45 so as to define a single rotation axis 4a for the sliders 41 and 42.

The first trajectory 45a and the second trajectory 46a may have a radius approximately equal or, as illustrated in FIG. 11, substantially smaller respectively to the first path 2a and to the second path 3a.

The second drag trajectory 46a has an inferior radius to the first drag trajectory 45a. In particular, the first 45a and the second drag trajectory 46a have respectively a radius approximately larger and smaller than the distance between the limbs 10.

The radius of the first drag trajectory 45a is approximately greater than 3 dm, in detail, substantially between 5 dm and 12 dm and, in more detail, approximately between 6 dm and 8 dm. Preferably, the radius of the first drag trajectory 45a is substantially equal to 7 dm.

The radius of the second drag trajectory 46a is approximately less than 5 dm, in detail, approximately less than 3 dm and, in more detail, approximately between 2 dm and 1 dm. Preferably, the radius of the second drag trajectory 46a is substantially between 1.5 dm and 1.6 dm.

It is to be noted how the drag trajectories 45a and 46a may both have the same radius or, alternatively, a different radius in relation to the acquisition paths 2a and 3a.

The movers 43 and 44 are suitable to define a stroke of the sliders 41 and 42 approximately at least equal to 180°, in particular, to 360°.

In addition they are suitable to move the sliders 41 and 42, and thus the modules 2 and 3 independently permitting a relative rotation between the modules 2 and 3, and/or in synchrony during, for example, a computerized tomography or other acquisition.

The first mover 43 comprises a first rack made along the first guide 45 and a first motorized gear wheel associated with the first slider 41 and engaged to said rack so as to control the movement of the first slider 41 along the first guide 45.

The second mover 44 comprises a second rack made along the second guide 46 and a second motorized gear wheel associated with the second slider 42 and engaged to said rack so as to control the movement of the second slider 42 along the second guide 46.

To enable the unit 4 located in the inner housing 7b to move the modules 2 and 3 resting on the surface 7a, the radiological imaging device 1 has at least one attachment suitable to constrain the modules 2 and 3 resting on the outer surface 7a to the unit 4 housed in the inner space 7b permitting said unit 4 to control the movement of the modules 2 and 3.

In particular, the at least one attachment defines an engagement position of the drive unit 4 to the modules 2 and 3 wherein the attachment constrains the unit 4 to the modules 2 and 3, enabling said drive unit 4 to drag the modules 2 and 3; and a disengaged position of the drive unit 4 from the modules 2 and 3 in which the attachment does not constrain the drive unit 4 to the modules 2 and 3, preventing the unit 4 from dragging the modules 2 and 3.

Preferably, the device 1 has a first attachment 8 suitable to constrain the first module 2 to the drive unit 4 and a second attachment 9 suitable to constrain the second module 3 to the drive unit 4.

More preferably the first attachment 8 is constrained to the first slider 41 and suitable to protrude from the platform 7 engaging the first module 2 and enabling the first module 2 to slide along the first drag trajectory 45a dragging the first module 2 along the first path 2a; while the second attachment 9 is constrained to the second slider 42 and suitable to protrude from the platform 7 engaging the second module 3 and enabling the second module 3 to slide along the second drag trajectory 46a dragging the second module 3 along the second path 3a. Alternatively, the first attachment 8 is constrained to the first module 2 and is suitable to engage the first slider 41; while the second attachment 9 is constrained to the second module 3 and is suitable to engage the second slider 42.

The first attachment comprises at least a first pin 81 and at least a first actuator suitable to move the pin 81 along a first direction approximately perpendicular to the surface 7a so that, in the engaged position, the first pin 81 protrudes from the outer surface 7a engaging in a seat of the first module 2 and, in the disengaged position, the pin 81 is outside said seat and, in particular, approximately entirely housed in the first slider 41.

Preferably, the first attachment 8 provides for several first pins 81, three in particular, suitably positioned along the arc of a circumference approximately concentric to the axis of rotation 4a and, preferably, of an approximately equal radius to the first acquisition path 2a.

The second attachment 9 comprises at least a second pin 91 and a second actuator suitable to move the second pin 91 in a second direction approximately perpendicular to the outer surface 7a so that, in the engaged position, the second pin 91 protrudes from the outer surface 7a engaging in a seat of the second module 3 and, in the disengaged position, the second pin 91 is outside said seat and, in particular, is approximately entirely housed in the second slider 42.

Preferably, the second attachment 9 comprises several second pins 91, three in particular, suitably positioned along the arc of a circumference approximately concentric to the axis 4a and, preferably, of a substantially equal radius to the second acquisition path 3a.

Optionally, the attachments 8 and 9 are suitable to absorb at least part of the weight of the modules 2 and 3 acting on the carriage wheels 23 and 33 and raising said modules from the surface 7a. Preferably, the attachments 8 and 9 are suitable to absorb approximately all the weight of the modules 2 and 3 and, in particular, to distance said modules from the surface 7a.

The outer surface 7a is substantially flat and preferably parallel to the floor surface 1a.

Its distance from the floor surface 1a is approximately between 0.5 and 3 dm and, in particular, between 1 dm and 2 dm.

The outer surface 7a has at least one area of analysis 7c (FIGS. 2, 4, 5, and 11) identifying a portion of outer surface 7a along the perimeter of which the modules 2 and 3 are movable and inside which the limb 10 being analyzed is positionable. The analysis area 7c is delimited by at least one through opening of the surface 7a defining the at least one acquisition path and suitable to permit the attachments 8 and 9, positioned in the housing 7b, to engage and guide the modules 2 and 3 resting on the surface 7a along the at least one acquisition path.

In particular, each analysis area 7c is delimited by an outer through opening 7d defining the first acquisition path 2a through which the first attachment 8 protrudes from the platform 7 engaging the first module 2 enabling the first slider 41 to guide the first module 2 along the first path 2a; and by an inner through opening 7e defining the second path 3a through which the second attachment 9 protrudes from the platform 7 and by constraining the second module 3 enables the second slider 42 to guide the second module 3 along the second acquisition path 3a.

The outer and inner through openings 7d and 7e have radii respectively approximately equal to the radii, above, of the paths 2a and 3a.

Figure 4:
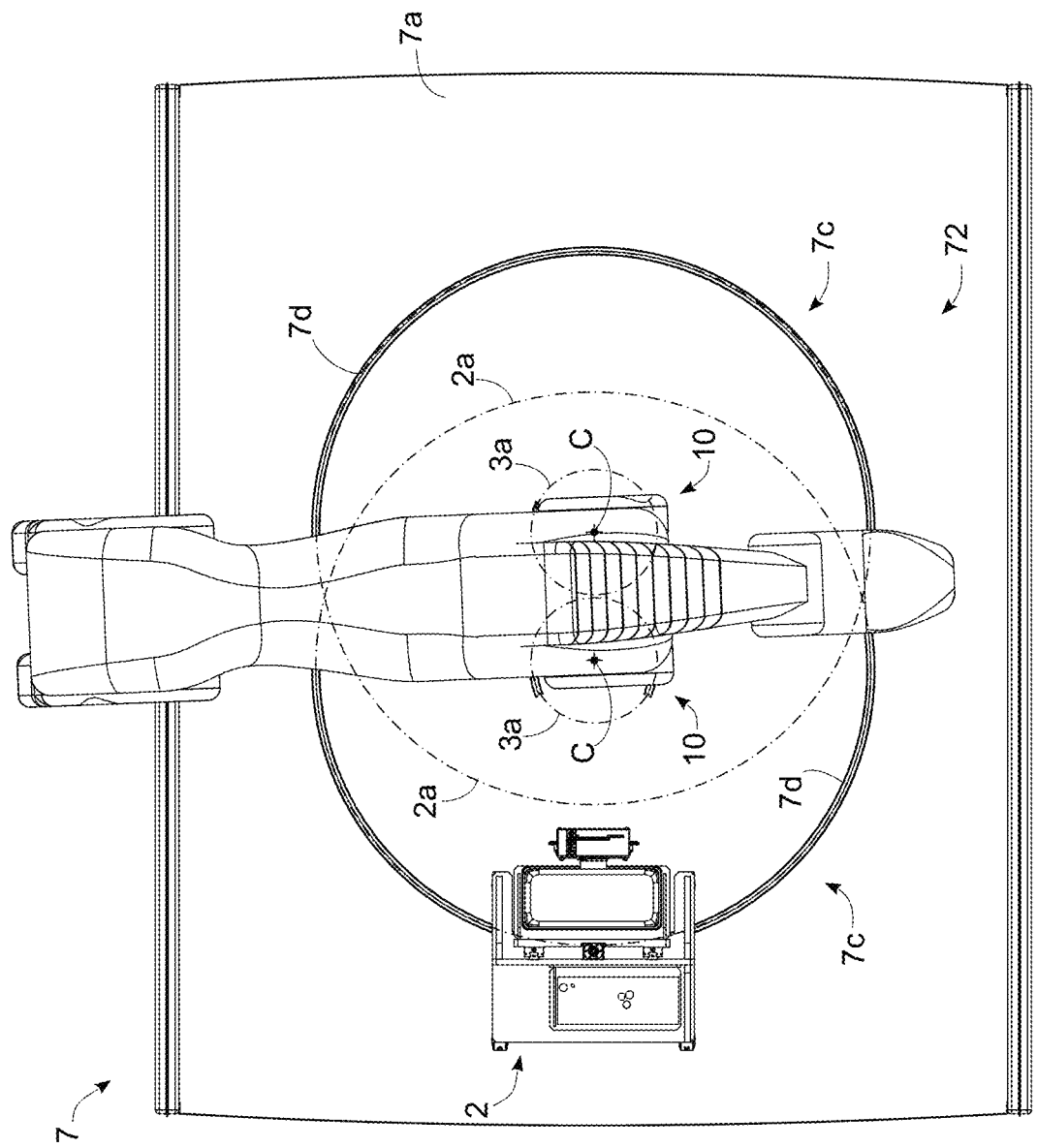
FIG. 4 shows a view from above of FIG. 2.

They are also concentric to each other in the analysis center C (FIGS. 4 and 11). The outer through opening 7d defines the amplitude of rotation of the first module 2 which may differ from the amplitude of rotation of the first slider 41. Similarly, the inner through opening 7e defines the amplitude of rotation of the second module 3 which may differ from the amplitude of rotation of the second slider 42.

The outer through opening 7d has an angular extension approximately at least equal to 180° and, in detail, approximately between 180° and 360° and, in more detail, between 190° and 250°. Preferably, the outer through opening 7d has an angular extension substantially at least equal to 220°.

The inner through opening 7e has an angular extension approximately at least equal to 180° and, in detail, substantially between 180° and 360° and, in more detail, between 190° and 250°. Preferably, the inner through opening 7e has an angular extension substantially at least equal to 220°.

Additionally, an analysis area 7c may provide a raised portion of the surface 7a identifying a support area for the limb 10 being analyzed characterized by a greater distance of the surface 1a from the surface 7a and thus the modules 2 and 3.

The raised portion is approximately flat and parallel to the outer surface 7a and, in particular, to the floor surface 1a.

Its distance from the surface 7a is substantially less than 2 dm, in detail, approximately between 0.1 dm and 1 dm and, more specifically, between 0.1 dm and 0.5 dm.

The distance between the raised portion and the floor surface 1a is approximately between 0.1 and 3.5 dm and preferably between 1 dm and 2.5 dm.

The portion has its center substantially positioned at said analysis Center C. To be precise, it is approximately circular, concentric to the outer and inner through openings 7d and 7e and, appropriately, has a radius substantially between 0.5 dm and 1 dm.

In some cases, the platform 7 is suitable to support several limbs 10 and may therefore may have a plurality of analysis areas 7c and thus have several through openings 7d and 7e defining several first paths 2a and several second paths 3a. Optionally, the outer through opening 7d and/or the inner through opening 7e of an analysis area 7c may have different radii respectively from the outer through opening 7d and from the inner through opening 7e so as to permit, for example, use of the device for animals of different sizes or for adults and children.

Preferably, it is suitable to support two limbs 10 and has two analysis areas 7c and thus two outer through openings 7d, two inner through openings 7e and optionally, two raised portions. The analysis centers C of said two analysis areas 7c are mutually distanced so that the second module 3 can slide on the surface 7a passing between the raised portions and thus the limbs 10. In detail, said distance is approximately less than 7 dm, preferably approximately less than 5 dm and, more preferably, approximately between 4 dm and 1.5 dm.

It is to be noted lastly how, in veterinary medicine, the platform 7 may provide for analysis areas 7c, one per limb 10.

The platform 7 comprises a plate 71 defining the outer surface 7a and separating said surface 7a from the internal housing 7b; a contouring 72 delimiting the housing 7b laterally; and, placed in the housing 7b, a support frame of the plate 7a.

It should be noted how the internal housing 7b, when the platform 7 is resting on the floor 1a, is delimited laterally by the contouring 72 and has one base identifiable in the plate 71 and the other in the floor 1a.

It may also provide for adjustable feet 73 suitable to come into contact with the floor surface 1*a* and to vary their extension to adjust the distance of the plate 61 from the floor 1*a*, and thus the extension of the housing 7*b*; and/or wheels, appropriately idle, to move the platform 7 and the unit 4 along the floor surface 1*a* and fitted with stops to block the wheels preventing the movement of the platform 7.

The plate 71 may provide closing flaps counter-shaped to the outer and inner through openings 7*d* and 7*e* and joined to the plate 71 so that when the attachments 8 and/or 9 protrude from the surface 7*a*, they flex, opening the outer or inner through opening 7*d* or 7*e* while, when, the attachments 8 and/or 9 do not protrude from the outer surface 7*a*, they superpose the outer or inner through opening 7*d* or 7*e*, closing it.

The plate may be covered in rubber or other high-friction material guaranteeing good adherence of the limb 10 to the outer surface 7*a*.

In the case of a single analysis area 7*c* constrained to the plate 71 or, preferably, to the contouring 72, the device 1 has the drive unit 4 placed with the axis of rotation 4*a* substantially passing through the analysis center C and thus through the center of the acquisition paths 2*a* and 3*a*.

In the case of multiple analysis areas 7*c*, the platform 7 comprises a conveyor 74 almost entirely placed inside the inner housing 7*b* and suitable to move the drive unit 4 in relation to the plate 71 defining multiple acquisition positions in each of which the axis of rotation 4*a* passes approximately through the center C of one of the analysis areas 7*c* thus superposing the attachments 8 and 9 over the outer and inner through openings 7*d* and 7*e* of same analysis area 7*c* (FIG. 11).

In particular, in the case of a radiological imaging device 1 with two areas of analysis 7*c*, the conveyor 74 is suitable to move along a sliding axis 74*a*, preferably substantially parallel to the outer surface 7*a*, the drive unit 4 defining two acquisition positions.

The conveyor 74 (FIGS. 8-9) comprises one or more linear guides 741, preferably two, defining the sliding axis 74*a*; and at least one carrier 742, suitably motorized, integral with the drive unit 4 and sliding along the guide 741.

In the case of a device 1 with four areas of analysis 7*c*, the conveyor 74 is suitable to move the unit 4 along two different axes 74*a* preferably approximately perpendicular to each other defining four acquisition positions, one for each analysis area 7*c*.

Lastly, the platform 7 may provide one or more sensors suitable to control the transition into the disengagement position of the attachments 7 and 8 when they detect any movements of the limb 10 from the surface 7*a*.

Said sensors may be optical sensors and thus film the analysis areas 7*c*. Alternatively, they may be pressure sensors (such as strain gage or piezoelectric) appropriately integrated into the plate 71 near the center of analysis C and suitable to control the transition into the disengagement position of the attachments 7 and 8 when they detect changes in weight on the analysis area 7*c*.

The control station 5 is suitable to allow the operator to control at least the operation of the device 1.

Figure 10:
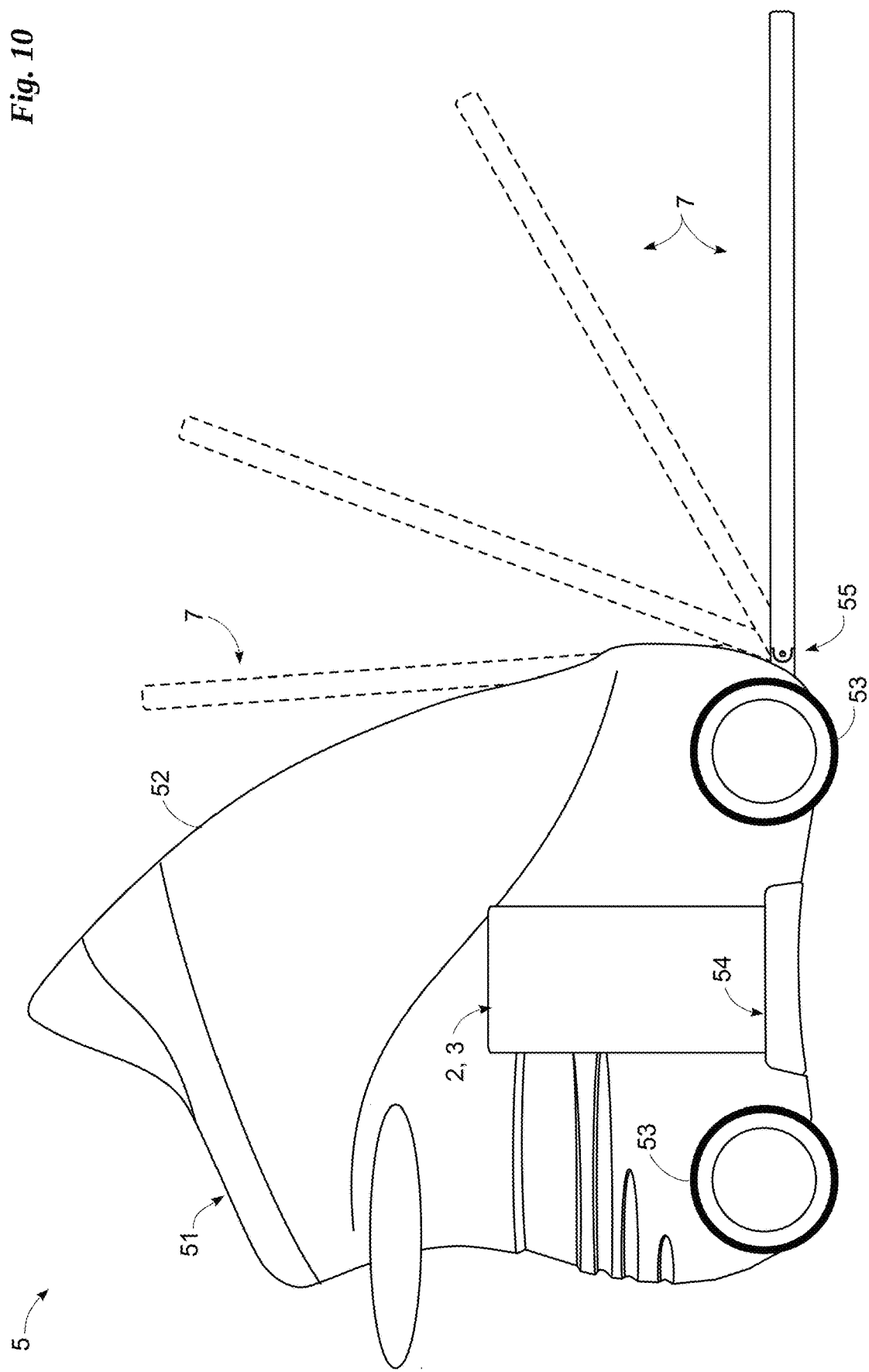
FIG. 10 is a schematic drawing of a part of the radiological imaging device.

As shown in FIGS. 1 and 10, it is identifiable in a body separate from the platform 7 and from the modules 2 and 3 and comprising interface means 51 (such as a keyboard, and/or a screen) by means of which the operator controls the acquisition and/or views the radiological images; a circuit board controlling the operation of the device 1; a memory for radiological images and/or patient data (age, acquisition parameters, etc.); a casing 52 defining the outer surface of the control station 5; movement means 53 (such as idle and/or motorized wheels) of at least the station 5; and power means of the device 1 such as a battery and/or connection cable to an external grid.

The control station 5 may further comprise at least one of the following: at least one coupling 54 suitable to constrain, preferably detachably, the modules 2 and 3 to the casing 52; a connecting member 55 of the platform 7 to the casing 52 and, appropriately, suitable to rotate around an axis approximately parallel to the outer surface 7*a*, the member 55 raising the platform 7 from the floor surface 1*a*. Preferably, the control station 5 comprises two couplings 54 constraining the two modules 2 and 3 to two different sides of the casing 52 and, placed in correspondence with a third side of the casing 22, the connecting member 55.

The connecting member 55 comprises forks, appropriately retractable, suitable to fit under the platform 7 which is thus appropriately forkable.

The connection apparatus 6 is suitable to allow a passage of data (i.e. electrical signals) and/or power between the control station 5 and the modules 2 and 3.

It is almost entirely placed under the surface 7*a* and, in particular, in the inner housing 7*b* and constrained to the platform 7.

The apparatus 6 comprises a static connector 61 suitable to carry power and/or data from the station 5 to the rotation axis 4*a*; at least one rotating connector suitable to carry power and/or data from the rotation axis 4*a* to at least one of the sliders 41 and 42 and integral with said at least one slider 41 and/or 42 so as to rotate together with it around the axis 4*a*; and at least one rotatory joint interposed between the static connector 61 and rotating connector and suitable to allow a passage of data and/or power between the connectors during their mutual rotation. In detail, the apparatus 6, shown in the enlargement of FIG. 7, comprises a static connector 61, a first rotating connector 62 integral with the first slider 41 and suitable to carry power and/or data from the rotation axis 4*a* to the first slider 41; a second rotating connector 63 integral with the second slider 42 and suitable to carry power and/or data from the axis 4*a* to the second slider 42; a rotary joint 64 connecting the static connector 61 to both the first rotating connector 62 and the second rotating connector 63.

The static connector 61 is at least partially inserted in the housing 7*b* and appropriately placed between the carrier 742 and floor 1*a*.

The connectors 62 and 63 and the rotatory joint 64 are almost entirely housed inside the inner housing 7*b* and, in particular, positioned between the carrier 742 and the plate 71.

The connectors 61, 62 and 63 are identifiable in hollow profiles, each of which provided with its own data transmission and/or power cables.

In this case, the rotatory joint 64 and 65 may provide one or more sliding contacts (or slip rings) suitable to connect the cables in the static connector 61 to those of the rotary connectors 62 and 63.

Each of these sliding contacts typically consists of a rotating conductive ring integral with one of the rotary connectors 62 or 63 and suitable to rotate around the rotation axis 4*a*; a static conductive ring integral with the static connector 61 and concentric to the previous ring, and contact means (for example, brushes) integral with the static ring which by rubbing on the rotating ring permit the passage of the signal and/or data during the rotation of the rotating ring with respect to the static ring and, thus, between the connector 61 and one of the connectors 62.

Preferably, the connection apparatus 6 provides for a first data and/or power cable 66 passing through the connectors 61 and 62 and a second data and/or power cable 67 passing through the connectors 61 and 63; and the rotary joint 64 is suitable to allow each cable 66 and 67 to rotate together with the relative rotating connector 63 and 64.

The rotary joint 64 (FIG. 7) comprises a first cylinder 641 integral with the static connector and defining a first chamber in which the first cable 66 in output from the static connector 61 enters; a first cap 642 of the first chamber integral with the first rotating connector 62 so as to enable the first cable 66 in output from the first chamber to pass into the first rotating connector 62; a second cylinder 643 housed and integral with the first cylinder 641 and defining a second chamber, inside the first chamber, in which the second cable 67 in output from the static connector 61 enters; a second cap 644 of the second chamber integral with the second rotating connector 63 and so that the second cable 67 in output from the second chamber passes into the second connector 63.

The first cap 642 is joined to the first cylinder 641 so as to rotate, commanded by the first connector 62, with respect to the first cylinder 641 and around the axis 4a allowing the first cable 67 to follow the rotation of the first connector 63.

The second cap 644 is joined to the first cap 642 so as to rotate, commanded by the second connector 63, with respect to said first cap 642 around the axis 4a allowing the second cable 67 to follow the rotation of the second rotating connector 63.

Moreover, the cables 66 and 67 are not constrained to the static connector 61 so that they are able to rotate on themselves avoiding twisting and, consequently, breaking.

For the passage of data between the first slider 41 and the first module 2, at least one of the first pins 81 may be of the electric type and, thus, realize both a mechanical connection and a data and/or power exchange between the slider 41 and module 2.

Similarly, for the passage of data between the second slider 42 and the second module 3, at least one of the second pins 91 may be of the electric type and, thus realize both a mechanical connection and a data and/or power exchange between the slider 42 and module 3.

Lastly, in the case of the second module 3 provided with a battery 35, the connection apparatus 6 may be devoid of the second connector 63, the second cylinder 643 and the second cap 644 and make a wireless connection, for example, Wi-Fi or Bluetooth, between the second module 3 and station 5.

In this case the connection apparatus 6 provides for an antenna integral with the second module 3 and an additional antenna associated with the station 5.

The functioning of a radiological imaging device for limbs, described above in a structural sense, is as follows.

Initially, the operator, through the interface means 51, commands the connecting member 55 to rotate the platform 7 resting it on the floor surface 1a, and then positions the limb 10 to be analyzed on the platform 7.

It is to be noted how the patient, human or animal, is placed on the platform 7 in an upright position and can thus position himself/itself on the surface 7a walking. For example, in the case of a horse, the operator makes the animal advance, bringing its front limbs 10 into the analysis area 7c.

In detail, to optimize the analysis, the operator places each limb 10 on the raised portions of the analysis areas 7c making sure that the barycentric longitudinal axis 10a is substantially centered with the center of analysis C.

At this point, the operator removes the modules from the station 5, resting them on the surface 7a at the outer and inner through openings 7d and 7e and, by means of the control station 5, orders the conveyor 74 to translate the drive unit 4 centering the rotation axis 4a with the center of analysis C and, therefore, with the longitudinal axis 10a of the limb 10 being analyzed.

The operator, again by means of the command station 5, orders the transition of the attachments 8 and 9 into the engaged position and thus, the constraint of the sliders 41 and 42 to the modules 2 and 3.

At this point, the operator selects the type of radiological imaging to be performed (for example, a computerized tomography), the extension, along the axis 10a, of the portion of limb 10 to be analyzed and the emission/acquisition parameters. After setting the acquisition, either automatically or in response to a command given by the operator via the means 51, the radiological imaging begins.

The sliders 41 and 42 slide on the guides 45 and 46 bringing the modules 2 and 3 into the acquisition start position placing the second module 3 between the limbs 10.

At the same time the translators 22 and 32 move the source 21 and detector 31 along the axes 22a and 32a bringing them to the correct height of the limb 10. After completing the positioning of the source 21 and of the detector 31, the source 21 emits the radiation which, passing only through the limb 10 being examined, hits the detector 31, while the sliders 41 and 43 rotate the modules 2 and 3 around the axes 4a and 10a and, thus, the limb 10 permitting completion of the acquisition and the video presentation of the image acquired.

Subsequently, the operator, if, for example, wishing to perform a linear X-ray, sets the emission/acquisition parameters and, thus, the device 1, automatically or in response to a command given by the operator, and starts the radiological imaging. In this case, the sliders 41 and 42 bring the modules 2 and 3 into the desired position, the source 21 emits the radiation which, passing only through the limb 10 being examined, hits the detector 31.

At the same time, the translators 22 and 32 move, substantially simultaneously, the source 21 and the detector 31 along the translation axes 22a and 32a performing the acquisition along the entire length of interest.

Lastly, it is to be noted that if, during these operations the animal moves one of the limbs on the surface 7a, the motion sensors detect the movement and, through the station 5, order the interruption of at least the emission and the transition of the attachments 8 and 9 into the disengagement position.

In order to have a complete description of the features and the function of the radiological imaging device 1 and, in addition, the advantages achieved by radiological imaging device is below described in terms of exemplary embodiments with reference to the drawings. These embodiments are not in contrast with the previous description and they are non-limiting exemplary embodiments. Furthermore, any features below described can be implemented in the radiological imaging device 1 above described and vice versa.

With reference to FIGS. 1-11, reference numeral 1 denotes a radiological imaging device. The radiological imaging device 1 is suitable for use in the veterinary and/or human field, to acquire radiological images of a limb 10 practically defining a barycentric longitudinal axis 10a. In detail, it is suitable to perform radiological imaging of the lower limbs of a human patient and of the front/rear limbs of an animal patient. More specifically, the imaging device 1 is utilizable in the veterinary sphere for producing radiological images of the front/rear limbs of a patient, such as, but not limited to a horse.

The radiological imaging device 1 is suitable to perform at least one of the following: radiography, computerized tomography, and fluoroscopy. Preferably, the device can perform an X-ray, a computerized tomography, and a fluoroscopy.

Figure 3:
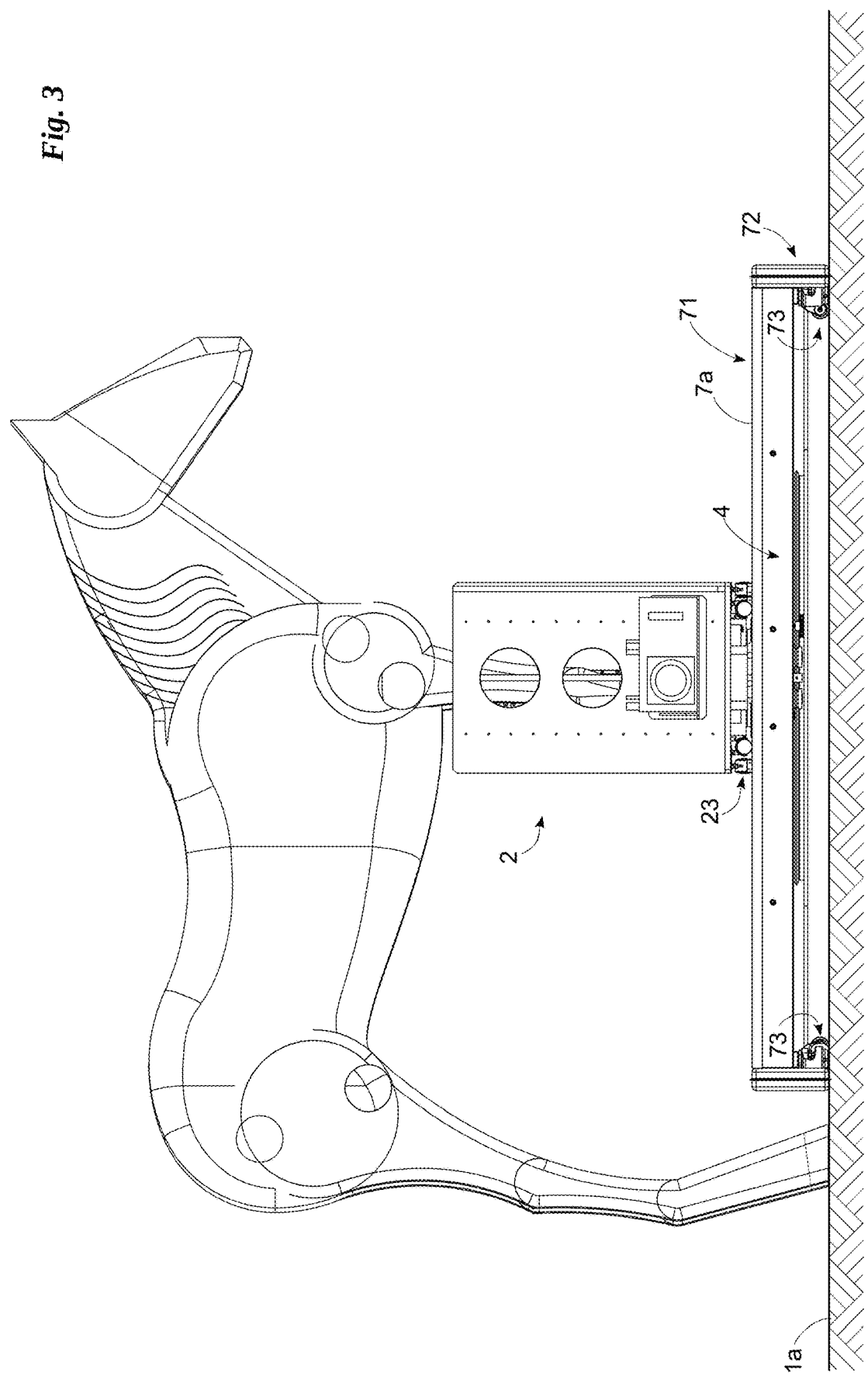
FIG. 3 shows a side view of FIG. 2.

In one embodiment, the radiological imaging device 1 includes, a first module 2 having a source 21 suitable to emit radiation defining an emission axis 21a. The device may also include a second module 3 suitable to be placed on the opposite side to the first module 2 with respect to the limb 10 being analyzed and having a detector 31 suitable to receive the radiation after it has passed through the limb 10 being analyzed. As shown in FIG. 3, the device includes a drive unit 4 capable of moving modules 2 and 3. The device also may include a control station 5 connected to the first and second modules 2 and 3 for controlling at least the acquisition and the movement of the modules 2 and 3. A connection apparatus 6 (see FIG. 5) is included in one embodiment to permit data and/or power exchange between the modules 2 and 3 and the control station 5. In this embodiment, the device includes a platform 7 that is suitable to be supported on a floor surface 1a and defining an outer support surface 7a for at least one limb 10 of the patient and the modules 2 and 3. The platform 7 also includes an inner housing 7b for housing at least a portion of the drive unit 4, as shown in the exemplary embodiment of FIG. 5.

In one embodiment, the first and second modules 2 and 3 are preferably supported by gravity on the outer support surface 7a and are suitable to slide on the surface 7a along at least one acquisition path passively. In this embodiment, the modules 2 and 3 are devoid of independent movement along the surface 7a and, therefore, the drive unit 4 moves the modules along surface 7a. The modules 2 and 3 may also be moved manually by an operator into position on the support surface 7a.

In an exemplary embodiment as shown in FIG. 4, the first module 2 may move or slide along a first acquisition path 2a that may be approximately circular. The second module 3 may move or slide along a second acquisition path 3a. The paths 2a and 3a may be substantially circular, however, in other embodiments, the paths may follow any shaped path. It has also been contemplated that the first and second modules 2 and 3 may be independently moved to any position on the outer support surface 7a, either mechanically or manually. As shown in FIG. 4, the paths 2a and 3a have distinct radii.

The second acquisition path 3a has an approximately distinct radius wherein it is less than the radius of the first acquisition path 2a in one embodiment. This is so the second module 3 and, thus the detector 31, are at a distance measured along the emission axis 21a (FIG. 7) from the limb 10 being analyzed, which is less than a distance measured along the emission axis 21a from the first module 2 and, thus of the source 21, to the limb 10 being analyzed.

By way of example only and not by way of limitation, the radius of the first path 2a is greater than approximately 3 dm (decimeters), and may be between approximately 5 dm and 12 dm. In another embodiment, the radius of the first path 2a may be between approximately 6 dm and 9 dm. Preferably, the radius of the first path 2a through outer through opening 7d (FIG. 6) may be equal to approximately 7 dm. Also, by way of example only, the radius of the second acquisition path 3a may be less than approximately 5 dm, and may be less than approximately 3 dm. In another embodiment, the radius of the second path 3a may be between approximately 2 dm and 1 dm. Preferably the radius of the second acquisition path 3a may be between approximately 1.5 dm and 1.6 dm.

In one embodiment, the first module 2 has a height less than approximately 12 dm. The height is measured perpendicular to the outer support surface 7a. The first module has a width less than approximately 10 dm, and the width is measured parallel to the outer support surface 7a and perpendicular to the emission axis 21a. Also, the first module 2 has a thickness of less than approximately 10 dm, and the thickness is measured along the emission axis 21a.

In other embodiments, the height of the first module 2 may be less than 10 dm and may be between approximately 8 dm and 7 dm. The width of the first module 2 may be less than approximately 7.5 dm and may be between approximately 5.5 dm and 4.5 dm. Also, the thickness of the first module 2 may be less than approximately 7.5 dm and may be between approximately 6 dm and 5 dm.

Figure 6:
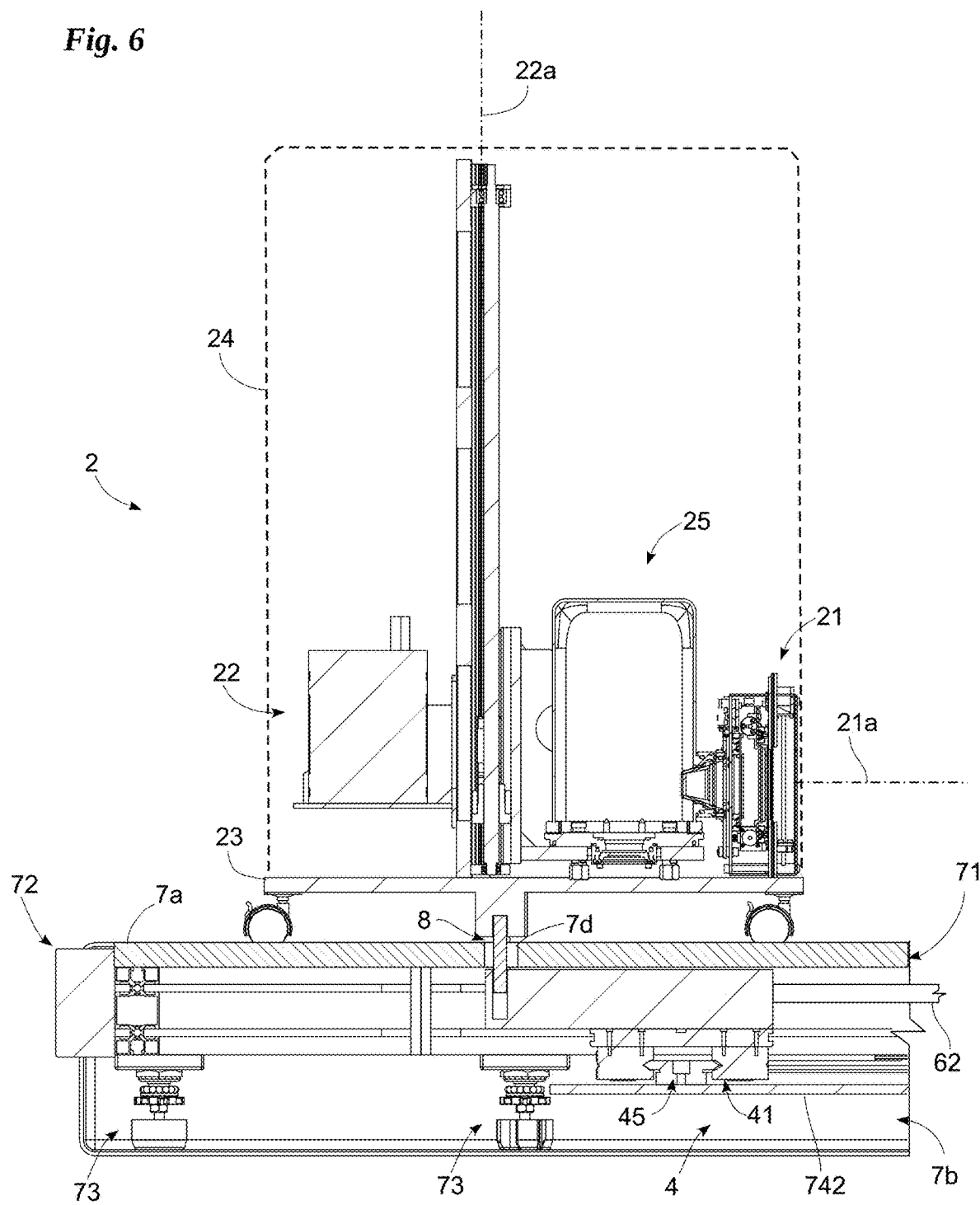
FIG. 6 shows a sub-assembly of FIG. 5.

As shown in the embodiment of FIG. 6, the first module 2 includes a source 21 suitable to emit radiation (e.g., ionizing radiation including X-rays or other types of radiation) defining an emission axis 21a preferably substantially parallel to the outer surface 7a. The first module 2 also includes a first translator 22 suitable to translate at least the source 21 along a first translation axis 22a approximately perpendicular to the outer support surface 7a. This embodiment also includes a first carriage 23 to which the source 21 and translator 22 are constrained and suitable to rest on the outer support surface 7a. There also may be a first casing 24 defining, together with the first carriage 23, a first containment space for at least the source 21 and the first translator 22. The first translation axis 22a is approximately perpendicular to the emission axis 21a as best shown in the example of FIG. 6.

In one embodiment, the first carriage 23 may be fitted with idler wheels or other structures suitable to permit the first module 2 to be idle in relation to the platform 7, i.e. able to slide or move along the surface 7a. The first casing 24 may be formed of a radiolucent material, such as a polymer, in particular, acrylonitrile butadiene styrene (ABS) to be crossed by the radiation emitted by the source 21. In one embodiment, the casing 24 may be at least partially formed of a radiolucent and damper material (foam) to be able to absorb impacts or other external stresses. Additionally, the first module 2 may include, housed in the first volume, at least one of the following: a cooling system 25 of the source 21; a collimator; a first linear actuator suitable to move the source 21 along the emission axis 21a varying the distance of the source 21 from the second module 3, and thus from the limb 10 being analyzed.

In one embodiment, the first module 2 includes at least the cooling system 25 and the collimator. Lastly, the first module 2 may include a cable holder chain suitable to enable electrical/data cables and/or pipes of the cooling system 25 to follow the source 21 during its translation along the axis 22a. The cooling system 25 may be integral with the source 21 so that the first translator 22 simultaneously translates the source 21 and the system 25. The collimator also may be integral with the source 21 in order to vary the direction and/or extent of the radiation, for example creating a "fan beam" or "cone beam" tomography or a linear X-ray.

The second module 3 is suitable to place itself between two limbs 10 of a patient (such as the lower limbs 10 of a human patient or the front or rear limbs 10 of a horse or other 10 animal) so that only the limb 10 being analyzed is between the modules 2 and 3. The second module 3 has a width or thickness less than approximately 4 dm, and the width or thickness is calculated along the emission axis 21*a* and is less than the distance between the two limbs 10 of the patient, i.e. in the case of a horse or the like, the distance is less than the minimum distance value between the carpals/metacarpals/fetlocks of the front and rear limbs. In another example, the width or thickness is less than approximately 3 dm. In one embodiment, the width or thickness of the second module 3 is between 1.5 dm and 2 dm. More specifically, the width or thickness may be approximately 2 dm and, in another embodiment, the width or thickness is approximately 1.5 dm.

The second module 3 has a height measured perpendicular to the support surface 7*a*. In one embodiment, the height of the second module 3 is less than approximately 12 dm. In another embodiment, the height is less than approximately 10 dm, and the height may be between 7 dm and 8 dm in another embodiment. In one embodiment, a width of the second module 3 measured parallel to the surface 7*a* and perpendicular to the emission axis 21*a* is less than approximately 10 dm. The width may be less than approximately 7.5 dm in one embodiment, and in another embodiment, the width of the second module 3 may be between approximately 4 dm and 5 dm.

Figure 7:
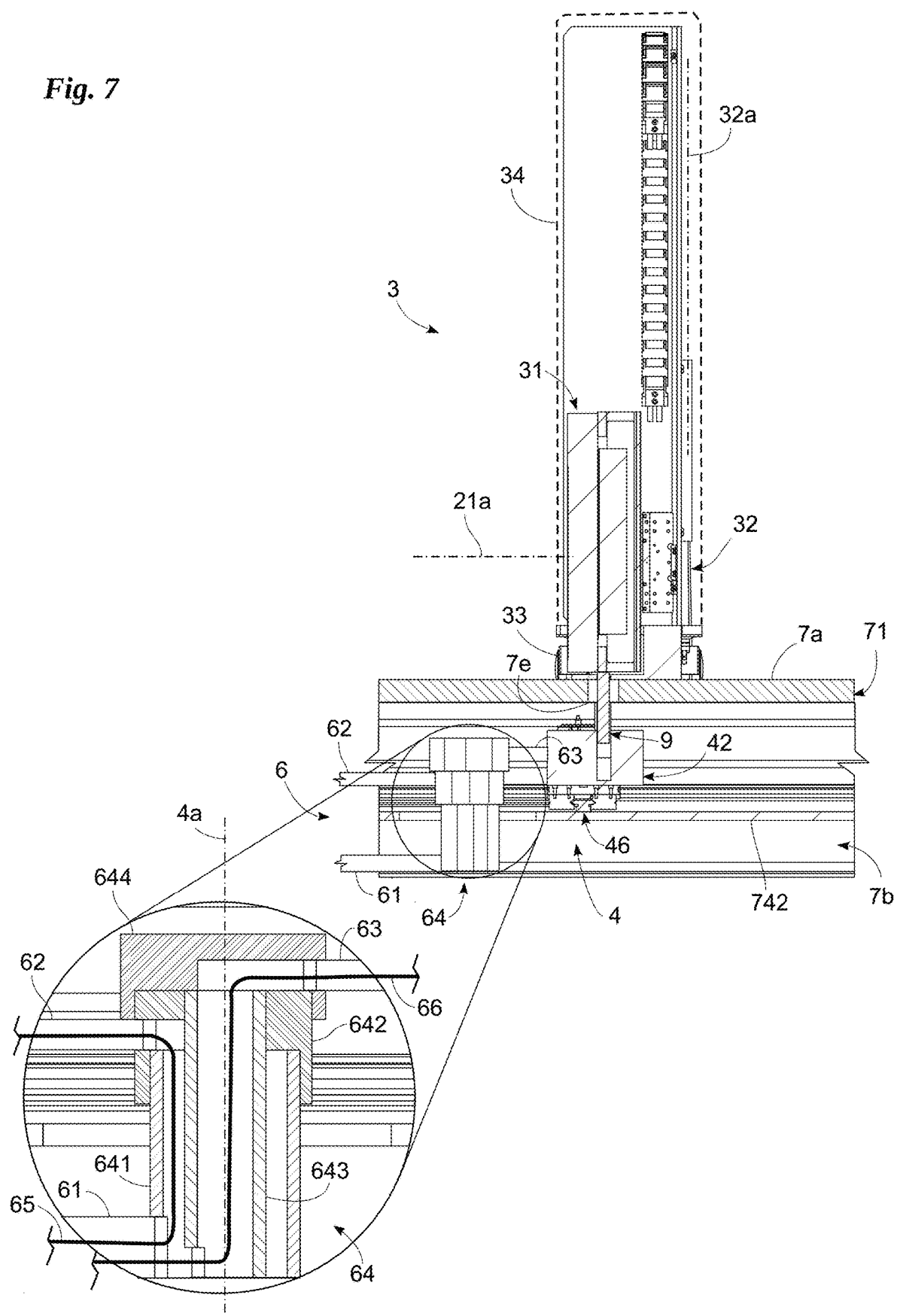
FIG. 7 is a second sub-assembly of FIG. 5.

As shown in the example of FIG. 7, the second module 3 includes a detector 31 suitable to receive the radiation after it has crossed the limb 10 being analyzed. Also, the second module 3 includes a second translator 32 suitable to translate the detector 31 along a second translation axis 32*a*, which is substantially perpendicular to the surface 7*a*. The second axis 32*a* also is approximately perpendicular to the emission axis 21*a*. Appropriately, the axes 22*a* and 32*a* are approximately parallel to each other and, to be precise, to the longitudinal axis 10*a* of the limb being analyzed. There may also be a second carriage 33 to which the detector 31 and the second translator 32 are constrained and suitable to rest on the outer surface 7*a*. A second casing 34 defining, together with the second carriage 33 a second containment space for at least the detector 31 and the second translator 32. In one embodiment, the second carriage 33 may include idler wheels or other means suitable to permit the second module 3 to be idle in relation to the platform 7, i.e. able to slide or move along the surface 7*a*.

By way of example only, the detector 31 is suitable to perform at least one of the following: radiography, computerized tomography, and fluoroscopy. The detector 31 may be able to perform an X-ray, computerized tomography, and fluoroscopy. In certain embodiments, the detector 31 includes a matrix sensor and may include a flat panel display.

In one embodiment, the second casing 34 is made of polymer material, such as acrylonitrile butadiene styrene (ABS) or other radiolucent material so as to be crossed by the radiation emitted by the source 21. In one embodiment, the second casing 34 is at least partially made of foam or a radiolucent and damper material so as to be able to absorb impacts or other external stresses.

In certain embodiments, the second module 3 includes, positioned in the second casing 34 and integral with the detector 31, at least one of the following: a battery 35 suitable to power at least the detector 31 and the second translator 32; and a second linear actuator suitable to translate the sensor 31 along the emission axis 21*a* by varying the distance between the sensor 31 and the limb 10 being analyzed. Furthermore, the second module 3 may include a cable holder chain suitable to enable electrical/data cables to follow the detector 31 during its translation 5 along the axis 22*a*.

In one embodiment, the modules 2 and 3 are passive, i.e. devoid of drives and movable only by the operator and/or by the drive unit 4. As shown in the figures, the drive unit 4 of one embodiment is placed within the inner housing 7*b*. The drive unit 4 may include at least one circular guide defining at least a circular drag trajectory of the rotation axis 4*a*. The rotation axis 4*a* is approximately perpendicular to the outer surface 7*a* and thus to the emission axis 21*a*. The rotation axis 4*a* may be approximately parallel to the translation axes 22*a* and 32*a*, and preferably, may be approximately concentric to the longitudinal axis 10*a* of the limb 10 being analyzed.

Figure 5:
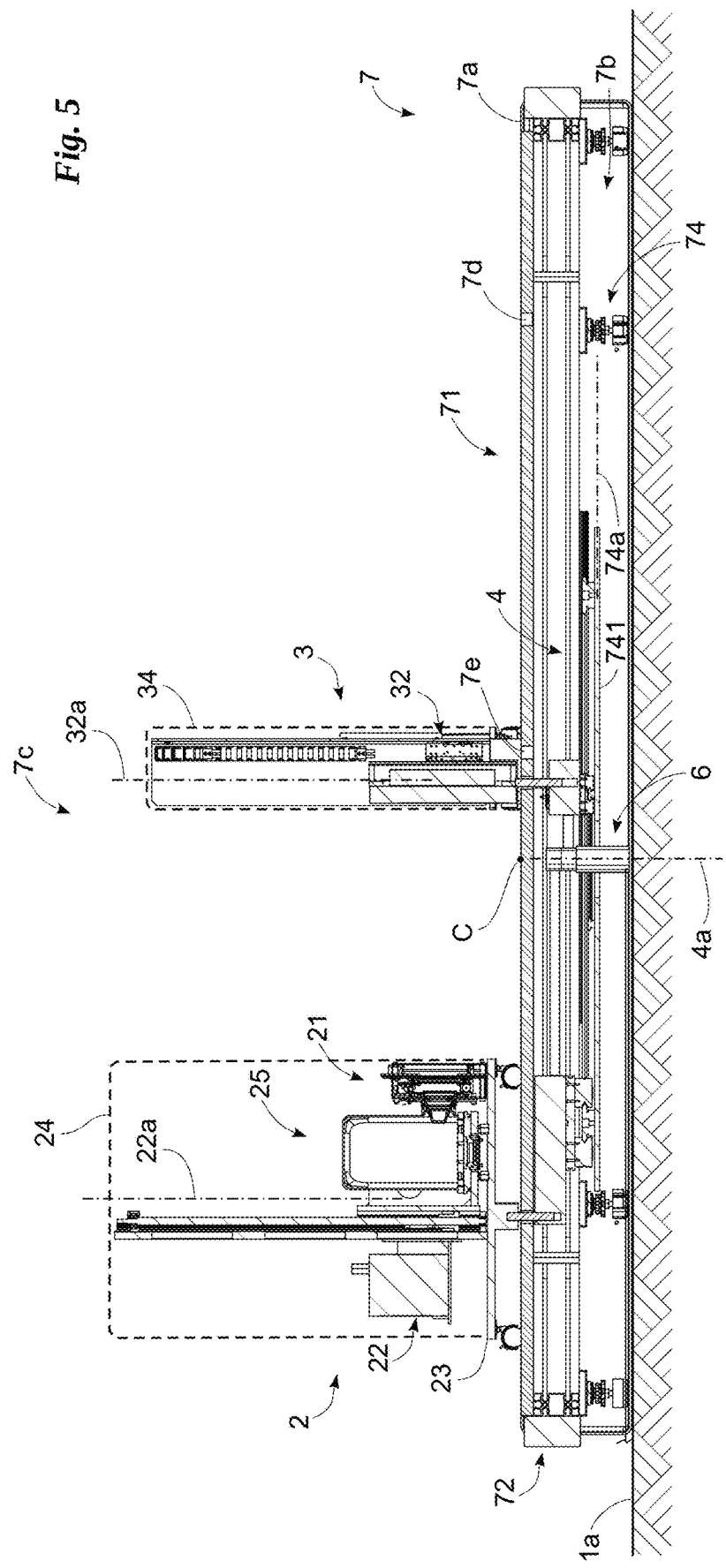
FIG. 5 shows a cross-section of an assembly of the radiological imaging device.
Figure 9:
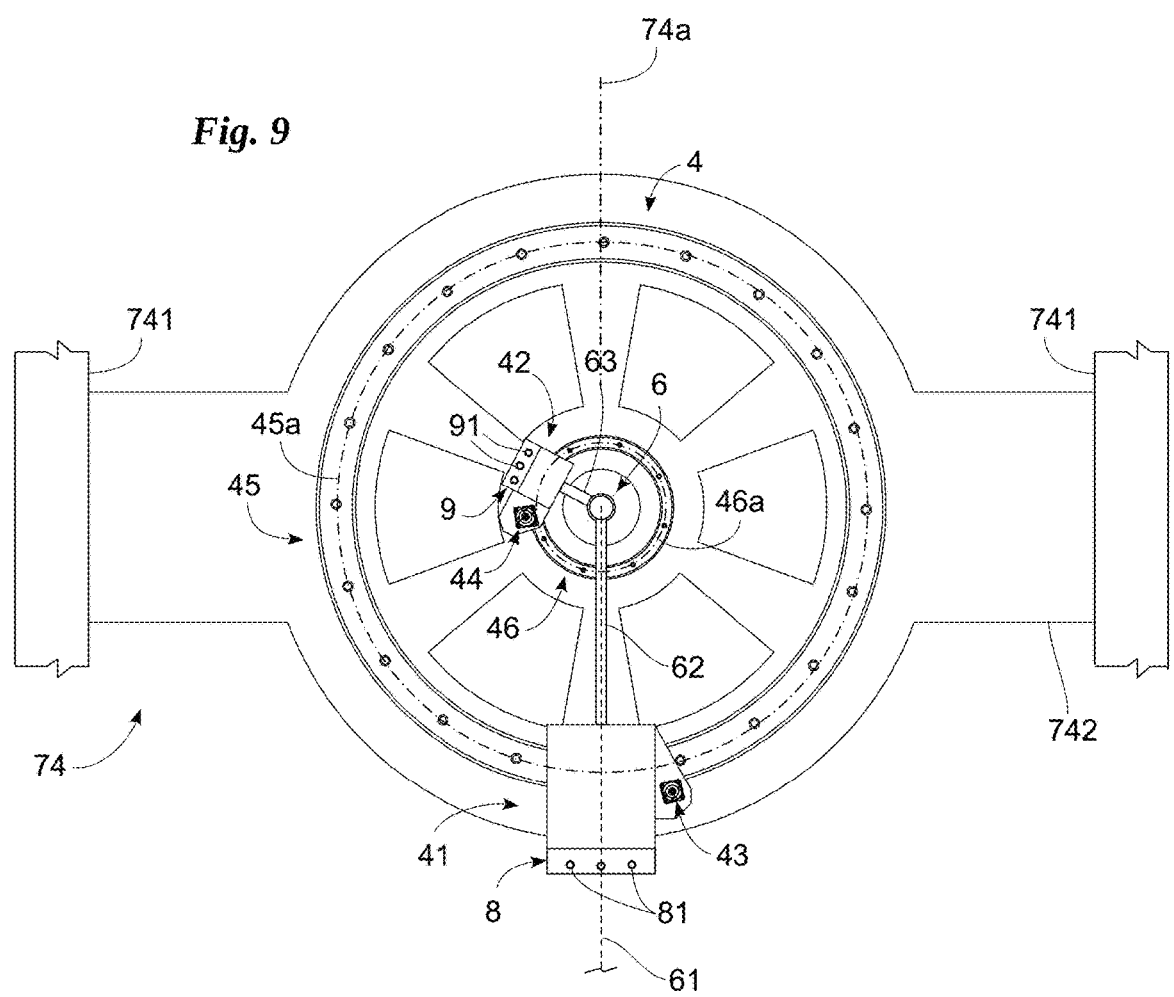
FIG. 9 is a part of the imaging device in FIG. 1.

Also, the drive unit 4 may include at least one slider suitable to slide along the circular guide and to be constrained to the modules 2 and 3. There may be at least one mover suitable to control the movement of the slider and thus of the modules 2 and 3. In one embodiment, the drive unit 4 includes a first slider 41 and a second slider 42 suitable to slide along the circular guide and to be respectively constrained to the first module 2 and to the second module 3. There also may be a first mover 43 and a second mover 44 suitable to control the movement respectively of the first slider 41 and of the second slider 42. As shown in the examples of FIGS. 4, 5, and 9, the drive unit 4 includes two different guides. The drive unit 4 may include a first circular guide 45 defining a first circular drag trajectory 45*a* with axis 4*a* and along which the first slider 41 slides dragging the first module 2. In addition, the drive unit 4 may include a second circular guide 46 defining a second circular drag trajectory 46*a* with axis 4*a*, distinct from the first drag trajectory 45*a* and along which the second slider 42 slides dragging the second module 3.

The second drag trajectory 46*a* is substantially concentric with the first guide 45 so as to define a single rotation axis 4*a* for the sliders 41 and 42. The first trajectory 45*a* and the second trajectory 46*a* may have a radius approximately equal or, as illustrated in FIG. 11, substantially smaller respectively to the first path 2*a* and to the second path 3*a*. In one embodiment, the second drag trajectory 46*a* has an inferior radius to the first drag trajectory 45*a*. In particular, the first 45*a* and the second drag trajectory 46*a* have respectively a radius approximately larger and smaller than the distance between the limbs 10 of the patient.

By way of example only, the radius of the first drag trajectory 45*a* is greater than approximately 3 dm, and may be between approximately 5 dm and 12 dm. In another embodiment, the radius of the first drag trajectory 45*a* is between approximately 6 dm and 8 dm. Preferably, the radius of the first drag trajectory 45*a* is substantially equal to 7 dm. Also, by way of example only, the radius of the second drag trajectory 46*a* is approximately less than 5 dm, and may be less than approximately 3 dm. In another embodiment, the radius of the second drag trajectory 46*a* is between approximately 1 dm and 2 dm. Preferably, the radius of the second drag trajectory 46*a* is between approximately 1.5 dm and 1.6 dm. It has been contemplated that the drag trajectories 45*a* and 46*a* may both have the same radius or, alternatively, a different radius in relation to the acquisition paths 2*a* and 3*a*.

In one embodiment, the movers 43 and 44 are suitable to define a stroke of the sliders 41 and 42 approximately at least equal to 180°, and in one embodiment approximately equal to 360°. In addition, the movers 43 and 44 are suitable to move the sliders 41 and 42, and thus the modules 2 and 3 independently permitting a relative rotation between the modules 2 and 3, and/or in synchrony during, for example, a computerized tomography or other acquisition.

The first mover 43 may include a first rack made along the first guide 45 and a first motorized gear wheel associated with the first slider 41 and engaged to the rack so as to control the movement of the first slider 41 along the first guide 45. The second mover 44 may include a second rack made along the second guide 46 and a second motorized gear wheel associated with the second slider 42 and engaged to the rack to control the movement of the second slider 42 along the second guide 46.

To enable the drive unit 4 located in the inner housing 7*b* to move the modules 2 and 3 resting on the surface 7*a* in one embodiment, the radiological imaging device 1 may have at least one attachment suitable to constrain the modules 2 and 3 resting on the outer surface 7*a* to the drive unit 4. The drive unit 4 may be housed in the inner space 7*b* permitting the drive unit to control the movement of the modules 2 and 3. In one embodiment, the at least one attachment defines an engagement position of the drive unit 4 to the modules 2 and 3 wherein the attachment constrains the drive unit 4 to the modules 2 and 3. This construction enables the drive unit 4 to drag or slide the modules 2 and 3. The at least one attachment may define a disengaged position, wherein the drive unit 4 is disengaged from the modules 2 and 3. In the disengaged position, the attachment does not constrain the drive unit 4 to the modules 2 and 3, preventing the unit 4 from dragging or sliding the modules 2 and 3. In one embodiment, the device 1 has a first attachment 8 suitable to constrain the first module 2 to the drive unit 4 and a second attachment 9 suitable to constrain the second module 3 to the drive unit 4.

In this embodiment, the first attachment 8 may be constrained to the first slider 41 and suitable to protrude from the platform 7 engaging the first module 2 and enabling the first module 2 to slide along the first drag trajectory 45*a* dragging the first module 2 along the first path 2*a*. Also, in this embodiment, the second attachment 9 may be constrained to the second slider 42 and suitable to protrude from the platform 7 engaging the second module 3 and enabling the second module 3 to slide along the second drag trajectory 46*a* dragging the second module 3 along the second path 3*a*. In an alternate embodiment, the first attachment 8 may be constrained to the first module 2 and be suitable to engage the first slider 41. In this alternate embodiment, the second attachment 9 may be constrained to the second module 3 and be suitable to engage the second slider 42.

By way of example only, the first attachment may include at least a first pin 81 and at least a first actuator suitable to move the pin 81 along a first direction approximately perpendicular to the surface 7*a* so that, in the engaged position, the first pin 81 protrudes from the outer surface 7*a* engaging in a seat of the first module 2. In the disengaged position, the pin 81 may be outside the seat and, in particular, approximately entirely housed in the first slider 41. In one embodiment, the first attachment 8 provides for several first pins 81, three in particular, suitably positioned along the arc of a circumference approximately concentric to the axis of rotation 4*a* and, preferably, of an approximately equal radius to the first acquisition path 2*a*.

Also by way of example only, the second attachment 9 may include at least a second pin 91 and a second actuator suitable to move the second pin 91 in a second direction approximately perpendicular to the outer surface 7*a* so that, in the engaged position, the second pin 91 protrudes from the outer surface 7*a* engaging in a seat of the second module 3. In the disengaged position, the second pin 91 is outside the seat and, in particular, is approximately entirely housed in the second slider 42. In one embodiment, the second attachment 9 may include several second pins 91, three in particular, suitably positioned along the arc of a circumference approximately concentric to the axis 4*a* and, preferably, of a substantially equal radius to the second acquisition path 3*a*.

In other embodiments, the attachments 8 and 9 are suitable to absorb at least part of the weight of the modules 2 and 3 acting on the carriage wheels 23 and 33 and raising the modules from the surface 7*a*. In one embodiment, the attachments 8 and 9 are suitable to absorb approximately all the weight of the modules 2 and 3 and, in particular, to distance the modules 2 and 3 from the outer support surface 7*a*.

The outer support surface 7*a* may be substantially flat and preferably parallel to the floor surface 1*a*. In one embodiment, the outer support surface 7*a* has a distance from the floor surface 1*a* between about 0.3 dm and 0.5 dm and, in particular, between about 1 dm and 2 dm.

The outer support surface 7*a* may have at least one area of analysis 7*c*, as shown in the examples of FIGS. 2, 4, 5, and 11, identifying a portion of outer surface 7*a* along the perimeter of which the modules 2 and 3 are movable and inside which the limb 10 being analyzed is positionable. The analysis area 7*c* is delimited by at least one through opening of the outer support surface 7*a* defining the at least one acquisition path and suitable to permit the attachments 8 and 9, positioned in the housing 7*b*, to engage and guide the modules 2 and 3 resting on the surface 7*a* along the at least one acquisition path.

In certain embodiments, each analysis area 7*c* is delimited by an outer through opening 7*d* defining the first acquisition path 2*a* through which the first attachment 8 protrudes from the platform 7 engaging the first module 2 and enabling the first slider 41 to guide the first module 2 along the first path 2*a*. Also, each analysis area 7*c* is delimited by an inner through opening 7*e* defining the second path 3*a* through which the second attachment 9 protrudes from the platform 7 and by constraining the second module 3 enables the second slider 42 to guide the second module 3 along the second acquisition path 3*a*. The outer and inner through openings 7*d* and 7*e* have radii respectively approximately equal to the radii above of the paths 2*a* and 3*a*. In this embodiment the outer and inner through openings 7*d* and 7*e* also are concentric to each other in the analysis center C as shown in FIGS. 4 and 11.

In one embodiment, the outer through opening 7*d* may define the amplitude of rotation of the first module 2, which may differ from the amplitude of rotation of the first slider 41. Similarly, the inner through opening 7*e* may define the amplitude of rotation of the second module 3, which may differ from the amplitude of rotation of the second slider 42. In certain embodiments, the outer through opening 7*d* has an angular extension at least equal to approximately 180° and, in detail, between approximately 180° and 360° and, in more detail, between approximately 190° and 250°. Preferably, the outer through opening 7*d* has an angular extension substantially at least equal to 220°. In certain embodiments, the inner through opening 7*e* has an angular extension at least equal to approximately 180° and, in detail, substantially between approximately 180° and 360° and, in more detail, between approximately 190° and 250°. Preferably, the inner through opening 7*e* has an angular extension substantially at least equal to 220°.

Additionally, an analysis area 7c may provide a raised portion of the surface 7a identifying a support area for the limb 10 being analyzed characterized by a greater distance of the surface 1a from the surface 7a and thus the modules 2 and 3. The raised portion may be approximately flat and parallel to the outer support surface 7a and, in particular, to the floor surface 1a. Its distance from the surface 7a is substantially less than 2 dm, in detail, the distance may be between approximately 0.1 dm and 1 dm and, more specifically, between approximately 0.1 dm and 0.5 dm. The distance between the raised portion and the floor surface 1a may be between approximately 0.1 and 3.5 dm and preferably between approximately 1 dm and 2.5 dm.

The portion has its barycenter substantially positioned at the analysis center C. In one embodiment, the analysis center is approximately circular, concentric to the outer and inner through openings 7d and 7e and, appropriately, has a radius between approximately 0.5 dm and 1 dm.

In some cases, the platform 7 is suitable to support several limbs 10 and may therefore have a plurality of analysis areas 7c with several through openings 7d and 7e defining several first paths 2a and several second paths 3a. In another embodiment, the outer through opening 7d and/or the inner through opening 7e of an analysis area 7c may have different radii respectively from the outer through opening 7d and from the inner through opening 7e so as to permit, for example, use of the device for animals of different sizes or for adults and children.

In one embodiment, it is suitable to support two limbs 10 and have two analysis areas 7c and thus two outer through openings 7d, two inner through openings 7e and optionally, two raised portions. The analysis centers C of the two analysis areas 7c are mutually distanced so that the second module 3 may slide on the outer support surface 7a passing between the raised portions and thus the limbs 10. In one embodiment, the distance is less than approximately 7 dm, and in another embodiment, the distance is less than approximately 5 dm and, may be between approximately 1.5 dm and 4 dm.

It has also been contemplated that in veterinary medicine, the platform 7 may provide for multiple analysis areas 7c, one per limb 10.

The platform 7 may include a plate 71 defining the outer surface 7a and separating the surface 7a from the internal housing 7b as shown in the embodiment of FIG. 6. There also may be a contouring 72 delimiting the housing 7b laterally; and, placed in the housing 7b, a support frame of the plate 7a. It should be noted that the internal housing 7b, when the platform 7 is resting on the floor 1a, is delimited laterally by the contouring 72 and has one base identifiable in the plate 71 and the other in the floor 1a.

In one embodiment, the platform 7 also may provide for adjustable feet 73 suitable to come into contact with the floor surface 1a and to vary their extension to adjust the distance of the plate 71 from the floor 1a, and thus the extension of the housing 7b. The platform 7 may include wheels alone or in combination with the adjustable feet 73. The wheels may move the platform 7 and the drive unit 4 along the floor surface 1a and be fitted with stops to block the wheels and prevent the movement of the platform 7.

In one embodiment, the plate 71 may include closing flaps counter-shaped to the outer and inner through openings 7d and 7e and joined to the plate 7. When the attachments 8 and/or 9 protrude from the surface 7a, the flaps flex, opening the outer or inner through opening 7d or 7e. Then, when, the attachments 8 and/or 9 do not protrude from the outer surface 7a, the flaps superpose the outer or inner through opening 7d or 7e closing it. It has also been contemplated that the plate 71 may be covered in rubber or other high-friction material guaranteeing good adherence of the limb 10 to the outer surface 7a. The plate 71 may be any material, including metal or plastic, and may further have imprints or marked patterns to provide additional traction for the limb 10.

In the embodiment having a single analysis area 7c constrained to the plate 71 or, preferably, to the contouring 72, the device 1 has the drive unit 4 placed with the axis of rotation 4a substantially passing through the analysis center C and thus through the center of the acquisition paths 2a and 3a.

In the embodiment of multiple analysis areas 7c, the platform 7 may include a conveyor 74 almost entirely placed inside the inner housing 7b. The conveyor 74 may be suitable to move the drive unit 4 in relation to the plate 71 defining multiple acquisition positions. In each of the multiple acquisition positions, the axis of rotation 4a passes approximately through the center C of one of the analysis areas 7c and, thus superposing the attachments 8 and 9 over the outer and inner through openings 7d and 7e of same analysis area 7c (FIG. 11).

Figure 8:
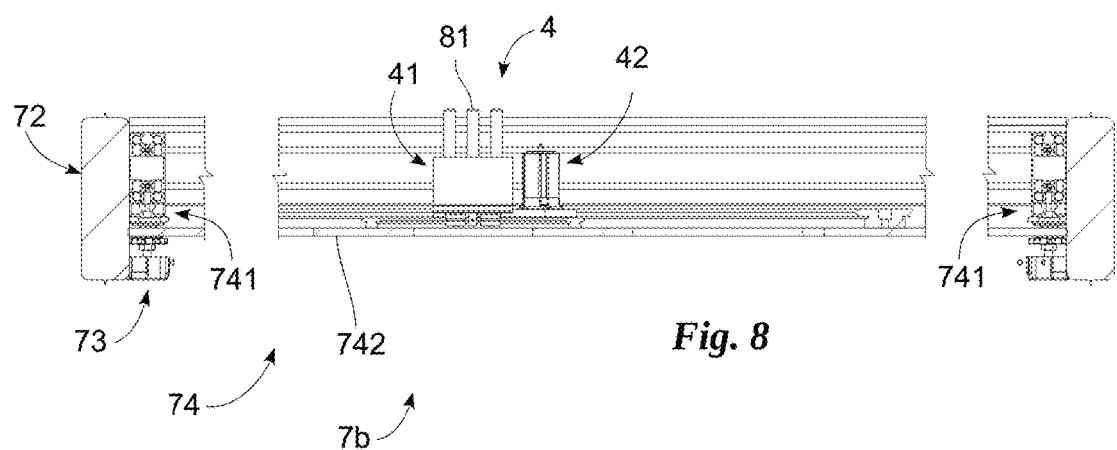
FIG. 8 shows a further sub-assembly of FIG. 5.

In particular, in the embodiment of a radiological imaging device 1 having two areas of analysis 7c, the conveyor 74 may be suitable to move along a sliding axis 74a, preferably substantially parallel to the outer surface 7a. The drive unit 4 may define two acquisition positions. As shown in the examples of FIGS. 8 and 9, the conveyor 74 may include one or more linear guides 741. In one embodiment the conveyor 74 includes two linear guides 741 defining the sliding axis 74a. The conveyor may include at least one carrier 742, suitably motorized, integral with the drive unit 4 and sliding along the guide 741.

In the embodiment of an imaging device 1 having four areas of analysis 7c, the conveyor 74 may be suitable to move the drive unit 4 along two different axes 74a, preferably approximately perpendicular to each other defining four acquisition positions, one for each analysis area 7c.

In yet another embodiment, the platform 7 may provide one or more sensors suitable to control the transition into the disengagement position of the attachments 7 and 8 when they detect any movements of the limb 10 from the surface 7a. The sensors may be optical sensors and thus film the analysis areas 7c. Alternatively, the sensors may be pressure sensors (such as strain gage or piezoelectric or the like) appropriately integrated into the plate 71 near the center of analysis C and suitable to control the transition into the disengagement position of the attachments 7 and 8 when they detect changes in weight on the analysis area 7c.

The control station 5 is suitable to allow an operator to control at least the operation of the imaging device 1. As shown in FIGS. 1 and 10, it is identifiable in a body separate from the platform 7 and from the modules 2 and 3. The control station 5 may include an input device or interface means 51 (such as a keyboard, mouse, track pad, touch screen, or display screen) that the operator uses to control the acquisition and/or views the radiological images. Further, a circuit board and/or processor controlling the operation of the imaging device 1 may also be included. The control station may include a memory for storing radiological images and/or patient data (age, acquisition parameters, etc.). A casing 52 defining the outer surface of the control station 5 may also be included. Furthermore, the control station 5 may include a movement apparatus 53 (such as idle and/or motorized wheels) to transport and move at least the station 5. The control station 5 may also include a power device or mechanism such as a battery and/or connection cable to an external grid.

In another embodiment, the control station 5 may include at least one coupling 54 suitable to constrain, preferably detachably, the modules 2 and 3 to the casing 52. The control station also may include a connecting member 55 of the platform 7 to the casing 52 and, appropriately, suitable to rotate around an axis approximately parallel to the outer surface 7a, the member 55 raising the platform 7 from the floor surface 1a.

In one embodiment, the control station 5 includes two couplings 54 constraining the two modules 2 and 3 to two different sides of the casing 52 and, placed in correspondence with a third side of the casing 22, the connecting member 55. The connecting member 55 includes forks, appropriately retractable, suitable to fit under the platform 7 which is thus appropriately forkable.

In one embodiment, the connection apparatus 6 is suitable to allow a passage of data (i.e. electrical signals) and/or power between the control station 5 and the modules 2 and 3. The connection apparatus may be at least partially placed under the surface 7a and, in particular, in the inner housing 7b and constrained to the platform 7. The connection apparatus 6 includes a static connector 61 suitable to carry power and/or data from the control station 5 to the rotation axis 4a. There may be at least one rotating connector suitable to carry power and/or data from the rotation axis 4a to at least one of the sliders 41 and 42 and integral with the at least one slider 41 and/or 42 so as to rotate together with it around the axis 4a. Further, the connection apparatus 6 includes at least one rotatory joint interposed between the static connector 61 and rotating connector and suitable to allow a passage of data and/or power between the connectors during their mutual rotation. In certain embodiments, the connection apparatus 6, shown in the enlargement of FIG. 7, includes a static connector 61, a first rotating connector 62 integral with the first slider 41 and suitable to carry power and/or data from the rotation axis 4a to the first slider 41. The connection apparatus 6 also includes a second rotating connector 63 integral with the second slider 42 and suitable to carry power and/or data from the axis 4a to the second slider 42. In addition, the connection apparatus 6 includes a rotary joint 64 connecting the static connector 61 to both the first rotating connector 62 and the second rotating connector 63. The static connector 61 is at least partially inserted in the housing 7b and appropriately placed between the carrier 742 and floor 1a. The connectors 62 and 63 and the rotatory joint 64 are almost entirely housed inside the inner housing 7b and, may be positioned between the carrier 742 and the plate 71.

The connectors 61, 62 and 63 are identifiable in hollow profiles, each of which may be provided with its own data transmission and/or power cables. In this case, the rotatory joint 64 and 65 may provide one or more sliding contacts (or slip rings) suitable to connect the cables in the static connector 61 to those of the rotary connectors 62 and 63. Each of these sliding contacts typically consists of a rotating conductive ring integral with one of the rotary connectors 62 or 63 and suitable to rotate around the rotation axis 4a. Further, the sliding contacts may include a static conductive ring integral with the static connector 61 and concentric to the previous ring. Contact apparatuses (e.g., brushes) may be integral with the static ring which by rubbing on the rotating ring permits the passage of the signal and/or data during the rotation of the rotating ring with respect to the static ring and, thus, between the connector 61 and one of the connectors 62.

In one embodiment, the connection apparatus 6 may provide for a first data and/or power cable 66 passing through the connectors 61 and 62 and a second data and/or power cable 67 passing through the connectors 61 and 63. The rotary joint 64 of the connection apparatus 6 may be suitable to allow each cable 66 and 67 to rotate together with the relative rotating connector 63 and 64. As shown in the example of FIG. 7, the rotary joint 64 includes a first cylinder 641 integral with the static connector and defining a first chamber in which the first cable 66 from the static connector 61 enters. The rotary joint 64 also includes a first cap 642 of the first chamber integral with the first rotating connector 62 to enable the first cable 66 from the first chamber to pass into the first rotating connector 62. A second cylinder 643 may be housed and integral with the first cylinder 641 and defining a second chamber, inside the first chamber, in which the second cable 67 from the static connector 61 enters. The rotary joint may include a second cap 644 of the second chamber integral with the second rotating connector 63 so that the second cable 67 from the second chamber passes into the second connector 63.

In one embodiment, the first cap 642 may be joined to the first cylinder 641 so as to rotate, commanded by the first connector 62, with respect to the first cylinder 641 and around the axis 4a. This allows the first cable 67 to follow the rotation of the first connector 63. The second cap 644 may be joined to the first cap 642 to rotate, commanded by the second connector 63, with respect to the first cap 642 around the axis 4a. This allows the second cable 67 to follow the rotation of the second rotating connector 63. Moreover, the cables 66 and 67 are not constrained to the static connector 61 so that they are able to rotate on themselves avoiding twisting and, consequently, breaking.

For the passage of data between the first slider 41 and the first module 2, at least one of the first pins 81 may be of the electric type and, thus realize both a mechanical connection and a data and/or power exchange between the slider 41 and module 2. Similarly, for the passage of data between the second slider 42 and the second module 3, at least one of the second pins 91 may be of the electric type and, thus realize both a mechanical connection and a data and/or power exchange between the slider 42 and module 3.

In yet another embodiment, if the second module 3 includes a battery 35, the connection apparatus 6 may be devoid of the second connector 63, the second cylinder 643 and the second cap 644 and make a wireless connection, for example, Wi-Fi or Bluetooth, between the second module 3 and the control station 5. In this embodiment, the connection apparatus 6 provides for an antenna integral with the second module 3 and an additional antenna associated with the control station 5.

The functioning of a radiological imaging device for limbs, described above in a structural sense, is as follows. Initially, the operator, through the interface 51, commands the connecting member 55 to rotate the platform 7 resting it on the floor surface 1a, and then positions the limb 10 to be analyzed on the platform 7. It is to be noted that the patient, human or animal, may be placed on the platform 7 in an upright position and can thus position himself/itself on the surface 7a walking. For example, in the case of a horse, the operator makes the animal advance, bringing its front limbs 10 into the analysis area 7c.

In one embodiment, to optimize the analysis, the operator places each limb 10 on the raised portions of the analysis areas 7c making sure that the barycentric longitudinal axis 10a is substantially centered with the center of analysis C. At this point, the operator may remove the modules from the control station 5, resting them on the surface 7a at the outer and inner through openings 7d and 7e. Then, using the control station 5, the operator orders the conveyor 74 to translate the drive unit 4 centering the rotation axis 4a with the center of analysis C and, therefore, with the longitudinal axis 10a of the limb 10 being analyzed.

The operator, again by interfacing with the command station 5, orders the transition of the attachments 8 and 9 into the engaged position and thus, the constraint of the sliders 41 and 42 to the modules 2 and 3. At this point, the operator selects the type of radiological imaging to be performed (for example, a computerized tomography), the extension, along the axis 10a, of the portion of limb 10 to be analyzed and the emission/acquisition parameters. After setting the acquisition, either automatically or in response to a command given by the operator via the interface 51, the radiological imaging begins.

The sliders 41 and 42 slide on the guides 45 and 46 bringing the modules 2 and 3 into the acquisition start position by placing the second module 3 between the limbs 10. At the same time the translators 22 and 32 move the source 21 and detector 31 along the axes 22a and 32a bringing them to the correct height of the limb 10. After completing the positioning of the source 21 and of the detector 31, the source 21 emits the radiation which, passing only through the limb 10 being examined, hits the detector 31, while the sliders 41 and 43 rotate the modules 2 and 3 around the axes 4a and 10a and, thus, the limb 10 permitting completion of the acquisition and the video presentation of the image acquired.

Subsequently, if the operator wishes to perform a linear X-ray, the operator may set the emission/acquisition parameters, and the imaging device 1 may automatically or in response to a command given by the operator start the radiological imaging. In this embodiment, the sliders 41 and 42 bring the modules 2 and 3 into the desired position, the source 21 emits the radiation which, passing only through the limb 10 being examined, hits the detector 31. At the same time, the translators 22 and 32 move, substantially simultaneously, the source 21 and the detector 31 along the translation axes 22a and 32a performing the acquisition along the entire length of interest.

It has been contemplated that if, during these operations the animal moves one of the limbs on the surface 7a, the motion sensors detect the movement and, through the control station 5, order the interruption of at least the emission and the transition of the attachments 8 and 9 into the disengagement position.

The current disclosure, see the both description of the radiological imaging device 1, achieves important advantages.

A first advantage is the ease of positioning a human or animal patient guaranteed by defining a support surface 7a. In fact, with the exception of the modules 2 and 3, the support surface 7a is free, and thus almost entirely accessible for positioning the patient. This advantage is defined by the innovative creation of an outer surface 7a on which to rest the modules 2 and 3 and an inner housing 7b which represents a separate environment from that of the positioning of the modules 2 and 3 and inside which to place the unit 4 and, later, the apparatus 6.

This advantage is further increased by the fact that the modules 2 and 3, being passive, i.e. devoid of a motor or other drive system along the outer surface 7a have particularly reduced dimensions.

Another advantage is given by the constraint of the platform 7 and of the modules 2 and 3 to the control station 5, which makes it possible both to reduce the overall dimensions of the radiological imaging device 1 and to move the entire radiological imaging device 1 acting from a single control station 5. As a result, the radiological imaging device 1 is simple and convenient to transport, even to a stable or other place difficult to access with the devices of the prior art.

Another advantage is the presence of the motion sensors that by detecting the movement of a limb 10 resting on the platform 7 disengage the sliders 41 and 42 from the modules 2 and 3 releasing them from the platform 7. Consequently, a possible collision of the limb 10 against one of the modules 2 and 3 neither wounds the animal or causes damage to the modules 2 and 3. This advantage is further guaranteed by the creation of the casings 24 and 34 in damping material and, thus able to absorb an impact avoiding damage to the instrumentation inside the module.

Variations may be made to the invention without departing from the scope of the inventive concept described in the independent claims and by the relative technical equivalents. All the details may be replaced with equivalent elements and the materials, shapes and dimensions may be as desired.

For example, in one embodiment, the first slider 41 may be identified in at least one ring sector. The first circular guide 45 may provide one or more idle pins hinged to the carrier 742 and defining a housing slot for the slider 41 spaced from the carrier 742 so as to keep the first slider 41 raised from the carrier 742. Also, the first mover 43 may include a rack made on the first slider 41 and a motorized toothed wheel connected to the carrier 742 and engaged with the rack.

Similarly, in one embodiment, the second slider 42 may be identified in at least one ring sector. The second guide 45 may provide one or more idle pins hinged to the carrier 742 and defining a housing slot for the second slider 42 spaced from the carrier 742 so as to keep the slider 42 raised from the carrier 742. The second mover 43 may include a rack made on the second slider 42 and a motorized toothed wheel connected to the carrier 742 and engaged with said rack.

In both cases, the ring sectors may have an angular extension equal to approximately 360°. The angular distance between adjacent pulleys may be substantially less than 180° and, in detail, substantially equal to 120°.

One of ordinary skill in the art will appreciate that not all radiological imaging systems have all these components and may have other components in addition to, or in lieu of, those components mentioned here. Furthermore, while these components are viewed and described separately, various components may be integrated into a single unit in some embodiments.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

The invention claimed is:

1. A radiological imaging device configured to analyze a limb, comprising:
    a first module including a source configured to emit radiation;
    a second module including a detector configured to receive radiation from the source that has passed through the limb;
    a control station connected to the first and second modules for controlling movement of the first and second modules and acquiring images from the second module; and
    a platform having an outer support surface to support the first and second modules, wherein the control station comprises a casing and a connecting member that is connected to the casing to attach the platform, the platform suitable to rotate around an axis approximately parallel to the outer surface,
    wherein the connecting member comprises retractable forks suitable to fit under the platform.

2. The device of claim 1, wherein the platform further comprises an inner volume and an analysis area and the device further comprises a drive unit housed within the inner volume of the platform and attached to the first and second modules.

3. The device of claim 2, further comprising a plurality of attachments configured to constrain the first and second modules to the drive unit.

4. The device of claim 3, wherein the plurality of attachments defines an engagement position wherein the plurality of attachments constrains the drive unit to the first and second modules allowing the drive unit to drag the first and second modules and a disengagement position wherein the plurality of attachments does not constrain the drive unit to the first and second modules preventing the drive unit from dragging the first and second modules.

5. The device of claim 4, wherein the platform includes a pressure sensor configured to order the transition into the disengagement position of the plurality of attachments when the pressure sensor detects changes in weight in the analysis area.

6. A radiological imaging device configured to analyze a limb, comprising:
    a first module including a source configured to emit radiation;
    a second module including a detector configured to receive radiation from the source that has passed through the limb;
    a control station connected to the first and second modules for controlling movement of the first and second modules and acquiring images from the second module;
    a platform having an outer support surface to support the first and second modules, wherein the platform comprises an inner volume and an analysis area and the device;
    a drive unit housed within the inner volume of the platform and attached to the first and second modules; and
    a plurality of attachments configured to constrain the first and second modules to the drive unit, the plurality of attachments defining an engagement position in which the plurality of attachments constrains the drive unit to the first and second modules allowing the drive unit to drag the first and second modules and a disengagement position in which the plurality of attachments does not constrain the drive unit to the first and second modules preventing the drive unit from dragging the first and second modules,
    wherein each of the plurality of attachments comprises an actuator to selectively place the plurality of attachments, respectively, in one of the engagement position and the disengagement position.

7. The device of claim 6, wherein the control station further comprises movement means.

8. The device of claim 7, wherein the movement means comprise wheels.

9. The device of claim 8, wherein the wheels are motorized.

10. The device of claim 8, wherein the wheels are non-motorized.

11. The device of claim 6, wherein each of the plurality of attachments each comprises one or more pins, and the actuator moves said one or more pins along a direction approximately perpendicular to the outer support surface, so that, in the engaged position, said one or more pins protrude from the outer support surface and, in the disengaged position, said one or more pins are approximately entirely housed in an inner volume of the platform.

12. The device of claim 11, wherein, in the engaged position, said one or more pins engage in a seat of a respective one of the first module and the second module.

* * * * *